(12) United States Patent
Zhang

(10) Patent No.: US 11,854,779 B2
(45) Date of Patent: Dec. 26, 2023

(54) SYSTEMS AND METHODS FOR REDUCING LAB-TO-LAB AND/OR INSTRUMENT-TO-INSTRUMENT VARIABILITY OF MULTI-ATTRIBUTE METHOD (MAM) BY RUN-TIME SIGNAL

(71) Applicant: AMGEN INC., Thousand Oaks, CA (US)

(72) Inventor: Zhongqi Zhang, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 595 days.

(21) Appl. No.: 16/972,742

(22) PCT Filed: Jun. 6, 2019

(86) PCT No.: PCT/US2019/035682
§ 371 (c)(1),
(2) Date: Dec. 7, 2020

(87) PCT Pub. No.: WO2019/236776
PCT Pub. Date: Dec. 12, 2019

(65) Prior Publication Data
US 2021/0265147 A1    Aug. 26, 2021

Related U.S. Application Data

(60) Provisional application No. 62/746,323, filed on Oct. 16, 2018, provisional application No. 62/763,110, filed on Jun. 8, 2018.

(51) Int. Cl.
*H01J 49/00* (2006.01)
*G01N 30/86* (2006.01)
*G01N 33/68* (2006.01)

(52) U.S. Cl.
CPC ...... *H01J 49/0009* (2013.01); *G01N 30/8665* (2013.01); *G01N 30/8696* (2013.01);
(Continued)

(58) Field of Classification Search
USPC .......................................... 702/121
See application file for complete search history.

(56) References Cited

U.S. PATENT DOCUMENTS 6,441,388 B1    8/2002    Thomas et al.
7,759,130 B2    7/2010    Oda et al.
(Continued)

FOREIGN PATENT DOCUMENTS

WO    2013/074861 A1    5/2013

OTHER PUBLICATIONS

Abbatiello, et al., Large-Scale Interlaboratory Study to Develop, Analytically Validate and Apply Highly Multiplexed, Quantitative Peptide Assays to Measure Cancer-Relevant Proteins in Plasma, Molecular & Cellular Proteomics, Sep. 1, 2015, American Society for Biochemistry and Molecular Biology, vol. 14, Nr.: 9, pp. 2357-2374, US.
(Continued)

*Primary Examiner* — Paul D Lee
(74) *Attorney, Agent, or Firm* — Amgen Inc.

(57) ABSTRACT

Systems and methods are described for reducing lab-to-lab and/or instrument-to-instrument variability of Multi-Attribute Methods (MAM) analyses via run-time signal intensity calibration. In various aspects, multiple MAM-based instruments each have detectors and different instrument conditions defined by different instrument models or sets of settings. Each MAM-based instrument receives respective samples and a reference standard as a calibrant. Each MAM-based instrument detects, via its detector, sample isoforms of its respective sample and reference standard
(Continued)

isoforms of the reference standard. The MAM-based instruments are associated with processor(s) that determine, via respective MAM iterations, correction factors and sample abundance values corresponding to the sample isoforms. The correction factors are based on the reference standard, and the sample abundance values are based on the correction factors. A variance value of the sample abundance values may be reduced based on correction factors of each of the MAM-based instruments.

22 Claims, 13 Drawing Sheets

(52) U.S. Cl.
CPC .......... *H01J 49/0036* (2013.01); *G01N 30/86* (2013.01); *G01N 33/68* (2013.01)

(56) References Cited

U.S. PATENT DOCUMENTS

| | | | |
|---|---|---|---|
| 8,633,031 | B2 | 1/2014 | Hunter |
| 11,031,217 | B2* | 6/2021 | Green ................... G01N 30/86 |
| 2008/0206737 | A1 | 8/2008 | Hunter |
| 2012/0187284 | A1* | 7/2012 | Geyer ................. H01J 49/0009 250/252.1 |
| 2013/0013273 | A1* | 1/2013 | Grothe, Jr. .......... H01J 49/0009 703/2 |
| 2014/0156202 | A1 | 6/2014 | Florida et al. |
| 2016/0035680 | A1 | 2/2016 | Wu |
| 2016/0356801 | A1 | 12/2016 | Glavina et al. |
| 2017/0045536 | A1 | 2/2017 | Butler et al. |

OTHER PUBLICATIONS

Liu, Y et al.: Linear model correction: A method for transferring a near-infrared multivariate calibration model without standard samples, Spectrochimica Acta Part A, vol. 169, Jun. 28, 2016 (Jun. 28, 2016), pp. 197-201.

Liu, Y et al.,Multi-spectrometer calibration transfer based on independent component analysis, Analyst, Jan. 30, 2018, Royal Society of Chemistry, UK, vol. 143, Nr.: 5, pp. 1274-1280, UK.

European Application 19814633 Supplementary European Search Report (dated Feb. 11, 2022) 10 pages.

Chilean Patent Application No. 202003182 Search Report (dated Feb. 22, 2022) 3 pages.

Liu, Y. et al: "Linear model correction: A method for transferring a near-infrared multivariate calibration model without standard samples", Spectrochimica Acta Part A, vol. 169, Jun. 28, 2016.

Liu et al et al: "Multi-spectrometer calibration transfer based on independent component analysis", Analyst, vol. 143, No. 5, Jan. 30, 2018.

Shaw et al., LC-MS/MS Peptide Mapping with Automated Data Processing for Routine Profiling of N-Glycans in Immunoglobulins, American Society for Mass Spectrometry, Mar. 25, 2014.

Ye et al., IgBLAST: an immunoglobulin variable domain sequence analysis tool, Nucleic Acids Research, 2013, vol. 41, Web Server Issue, May 13, 2013.

Office Action, Japanese Patent Application No. 2020-566732 (dated Feb. 21, 2023).

TW Application 108119640, Office Action (dated Mar. 27, 2023).

* cited by examiner

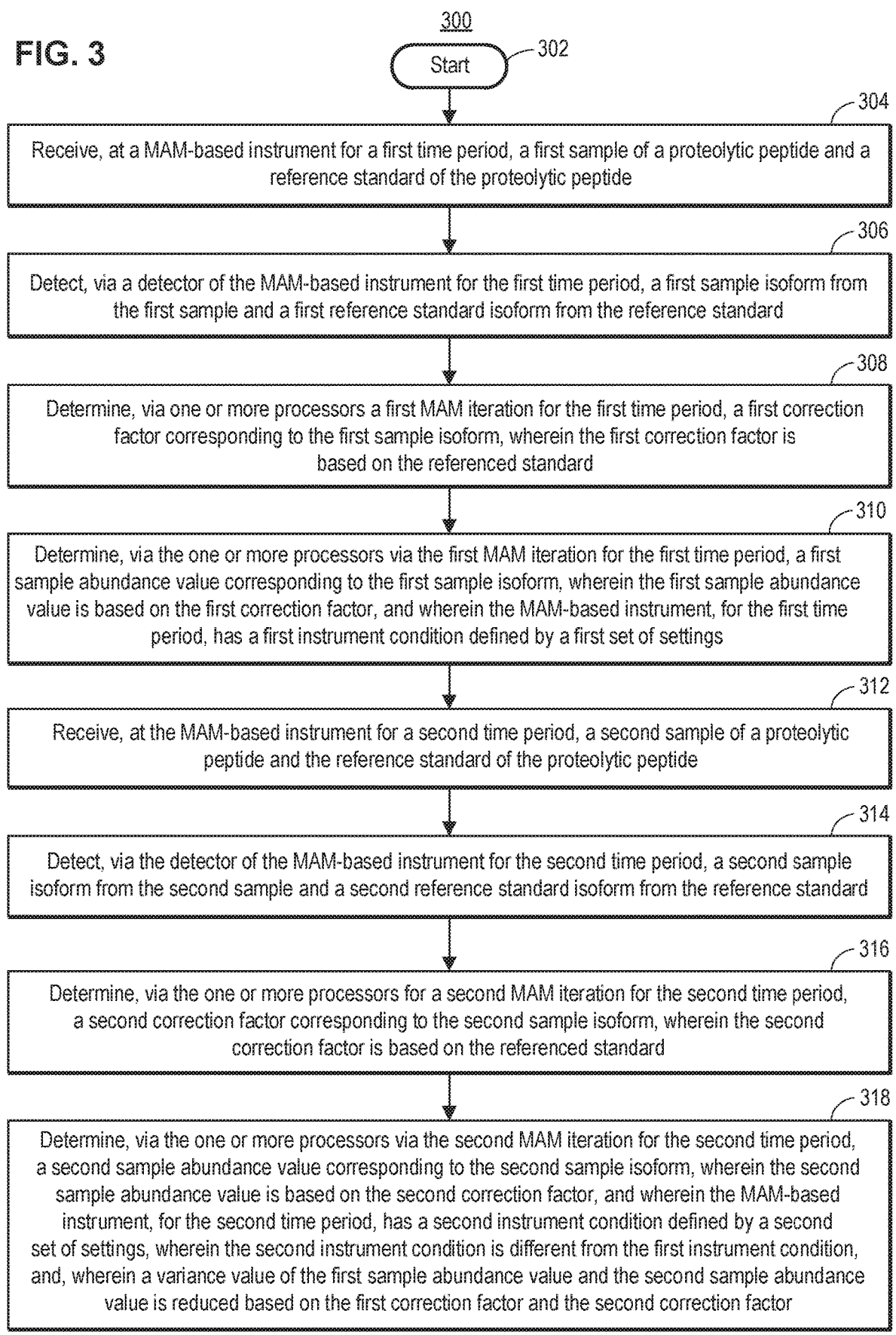

SYSTEMS AND METHODS FOR REDUCING LAB-TO-LAB AND/OR INSTRUMENT-TO-INSTRUMENT VARIABILITY OF MULTI-ATTRIBUTE METHOD (MAM) BY RUN-TIME SIGNAL

CROSS REFERENCE TO RELATED APPLICATIONS

This application is a national stage application under 35 U.S.C. § 371 of International Application No. PCT/US2019/035682, having an international filing date of Jun. 6, 2019; which claims the benefit under 35 U.S.C. 119(e) of U.S. Provisional Application No. 62/763,110, filed Jun. 8, 2018; and U.S. Provisional Application No. 62/746,323, filed Oct. 16, 2018, all of which are incorporated by reference herein in their entireties.

FIELD OF THE DISCLOSURE

The present disclosure generally relates to reducing lab-to-lab and instrument-to-instrument variability of multi-attribute method (MAM) via run-time signal intensity calibrations.

BACKGROUND

Biotherapeutic development typically includes monitoring certain attributes of therapeutic molecule(s), where such attributes are identified as critical quality attributes (CQAs) for the purposes of measuring product safety and efficacy. Mass spectrometry (MS) can be used in assays for measuring the quality attributes. Generally, MS refers to an analytical technique that ionizes chemical species and sorts the ions based on their mass-to-charge ratio. In this manner, an MS device can measure the mass of a molecule within a sample. In the case of polypeptide attributes, use of mass spectrometry allows for the assessment of more quality attributes using fewer analyses.

MS can be used to monitor post-translational modifications (PTMs), including glycosylation profiles, and/or excipients using both ultraviolet (UV) and mass data by implementing multi-analyte/attribute, or so-called Multi-Attribute Methods (MAMs). The MAM uses a combination of MS data and automated identification and relative quantification of attributes (Rogers, R S, et al. 2015. Development of a quantitative mass spectrometry multi-attribute method for characterization, quality control testing and disposition of biologics. mAbs 7:5, 881-890). Because of efficiency and quality control benefits, MAM is increasingly being used with MS, for example, to provide increased selectivity, sensitivity, and flexibility to quality attribute analysis. MAM refers to an analytical approach that can quantify multiple product and process attributes (e.g., quality attributes/CQAs), within a single analysis. For example, MAM-based assays are typically targeted towards monitoring downstream processes, but they are increasingly used for quality control assays for lot (e.g., sample) release as well.

For example, a MAM procedure, based on proteolytic digestion followed by Liquid Chromatography (LC)/MS analysis of proteolytic peptides (peptides are fragments of a larger polypeptide that are produced by proteolysis), can be used to quantify a variety of quality attributes for therapeutic proteins. The procedure takes advantage of the resolving power provided by a mass spectrometric detector and can use the MS intensity of each isoform (including the modified and unmodified form) of a proteolytic peptide for quantitation.

Incorporation of mass spectrometry with MAM can create challenges, because MS procedures typically require highly trained analysts and a significant lab infrastructure. In particular, a major challenge of mass spectrometry-based MAM analysis is the observed high variability of prepared samples used within a laboratory and of different instruments in those labs. For example, sample preparation variability may arise from different lab analysts who prepare samples in different manners that result in differences between the prepared samples. For example, after a sample is received, a lab analyst typically performs a complicated procedure (e.g., proteolytic digestion) to prepare the sample for injection. Due to the complexity of the procedure, prepared samples can be quite variable, even if the original sample is consistent. The sample preparation procedure, due to its long duration, can introduce modifications that change abundance of various attributes. These artificial modifications cause inaccuracies and variations in the MAM result. Different digestion efficiencies during sample preparation by lab analysts also contribute to variability between labs. Variability can also arise from lab instruments using different settings or executing different models of operation. Currently, to ensure reproducible attribute measurements, not only must a similar instrument model be used by all analytical laboratories, the instrument must also be tuned to the same conditions. However, constraining labs to a specific model may also restrain labs from upgrading their equipment to take advantage of the most recent advances.

Challenges of MS-MAM-based analysis also arise from assumptions and approaches used in conventional MAM procedures. For example, in a conventional MS-MAM procedure, the abundance of each attribute (e.g., the different modification state of an amino acid residue in a peptide) is determined based on the MS responses (e.g., peak areas) of the modified peptide and the unmodified peptide with the following assumptions: (1) unmodified and modified peptides have reproducible recovery between labs; (2) unmodified and modified peptides have the same MS response factor, and (3) artificially induced attribute changes are negligible.

Due to these assumptions, a conventional MAM procedure depends on multiple required conditions, including that (1) the digestion efficiency is reproducible between labs; (2) the MS instrument conditions are exactly the same; and (3) the sample preparations performed by different labs introduce minimal or a constant amount of artificial modifications. In reality, however, these required conditions are difficult to meet because of variations of sample preparation procedures, analyst habits, instruments, reagent quality, etc. Peptide recovery can also fluctuate, causing additional variability.

Additional challenges of meeting the required conditions include differences in MS instrument model or instrument settings. For example, the manner in which one lab instrument is maintained can differ from the manner in which a second lab instrument lab is maintained. In addition, a response factor for peptides containing different variants across different labs may differ. Further challenges of meeting the required conditions include variations of sample preparation procedure, analyst habit, device and reagent quality, as well as instrument condition. In addition, the amount of artificially introduced modification may vary.

As a result, conventional MS-based MAM methods lack robustness in lab-to-lab and/or instrument-to-instrument variability.

In addition, a major challenge of mass spectrometry-based multi-attribute method (MAM) is its high variability between analysts and instruments. For reproducible attribute measurements, not only a similar instrument model is required for all analytical labs, the instrument must also be tuned to the same condition. This poses great long-term challenges, considering the rapid development of new chromatography and mass spectrometry technologies. In addition, difference in digestion efficiency and artificial modifications (e.g., oxidation, deamidation, Asp-isomerization, and fragmentation) during sample preparation also contribute to variability between laboratories. These challenges must be resolved to ensure a long-term success of MAM, e.g., in a cGMP environment.

BRIEF SUMMARY

Hence, there is a need for systems and methods for reducing lab-to-lab and/or instrument-to-instrument variability of MS-based multi-attribute method (MAM)) via run-time signal intensity calibrations.

As described herein, system and methods are disclosed for reducing lab-to-lab and/or instrument-to-instrument variability of multi-attribute method (MAM) via run-time signal intensity calibrations. As described for various embodiments, the systems and methods may be used to determine attribute abundance in a sample (e.g., sample abundance values of each quality attribute) using measured or known attribute abundance in a reference standard (e.g., reference standard abundance values of each quality attribute) as a calibrant. This new technique increases lab-to-lab and/or instrument-to-instrument efficiency and allows for reduced variability among labs and/or instruments. For example, this new technique requires no or minimal additional work from an analyst or lab because reference standard data is typically collected for MAM analysis. This is because, for a typical MAM procedure, the reference standard is analyzed in parallel with samples for other purposes, e.g., system suitability and identity purpose. In addition, using the reference standard as a calibrant is further beneficial because, in the reference standard, most quality attributes remain constant throughout the life of the standard, and, therefore the reference standard can be used as calibrant, in a unique way, to correct for difference between instruments or sample preparation procedures.

In various embodiments described herein, systems and methods are described for reducing lab-to-lab or instrument-to-instrument variability of MAM analyses via run-time signal intensity calibration. For example, for some embodiments, such systems and methods may include a first MAM-based instrument including a first detector. The first MAM-based instrument can have a first instrument condition defined by at least one of (1) a first instrument model or (2) a first set of settings. The first MAM-based instrument can be configured to receive a first sample and a reference standard. The first MAM-based instrument can be further configured to, via the first detector, detect a first sample isoform from the first sample and a first reference standard isoform from the reference standard.

The systems and methods can further include one or more processors associated with the first MAM-based instrument. The one or more processors associated with the first MAM-based instrument can be configured to determine, via a first MAM iteration, a first set of correction factors corresponding to the first sample isoform. The first set of correction factors can be based on the reference standard. The one or more processors associated with the first MAM-based instrument can be further configured to determine a first set of sample abundance values corresponding to the first sample isoform, where the first set of sample abundance values is based on the first set of correction factors.

The systems and methods can further include a second MAM-based instrument including a second detector. The second MAM-based instrument can have a second instrument condition defined by at least one of: (1) a second instrument model or (2) a second set of settings.

In various embodiments, the second instrument condition can be different from the first instrument condition.

The second MAM-based instrument can be configured to receive a second sample and the reference standard. The second MAM-based instrument can be further configured to, via the second detector, detect a second sample isoform from the second sample and a second reference standard isoform from the reference standard.

The systems and methods can further include one or more processors associated with the second MAM-based instrument. The one or more processors associated with the second MAM-based instrument can be configured to determine, via a second MAM iteration, a second set of correction factors corresponding to the second sample isoform. The second set of correction factors can be based on the reference standard. The one or more processors associated with the second MAM-based instrument can be further configured to determine a second set of sample abundance values corresponding to the second sample isoform, where the second set of sample abundance values is based on the second set of correction factors.

Based on the correction factors determined for each instrument, variability of measurements can be reduced between the first MAM-based instrument and second MAM-based instrument. For example, a variance value of the first set of sample abundance values and the second set of sample abundance values can be reduced based on the first set of correction factors of the first MAM-based instrument and the second set of correction factors of the second MAM-based instrument.

In additional embodiments, calibration systems and methods are disclosed for reducing variability of a MAM-based instrument for multiple time periods via run-time signal intensity calibration. In such embodiments, a MAM-based instrument, for a first time period, can receive a first sample and a reference standard.

The MAM-based instrument can detect, via a detector for the first time period, a first sample isoform from the first sample and a first reference standard isoform from the reference standard.

One or more processors can be configured to, via a first MAM iteration for the first time period, determine a first set of correction factors corresponding to the first sample isoform, where the first set of correction factors is based on the reference standard.

The one or more processors can also be configured to determine, via the first MAM iteration and for the first time period, a first set of sample abundance values corresponding to the first sample isoform. The first set of sample abundance values can be based on the first set of correction factors. The MAM-based instrument, for the first time period, can have a first instrument condition defined by a first set of settings.

The MAM-based instrument, for a second time period, can be configured to receive a second sample and a reference standard.

The MAM-based instrument can detect, via the detector for the second time period, a second sample isoform from the first sample and a second reference standard isoform from the reference standard.

The one or more processors can be configured to, via a second MAM iteration for the second time period, determine a second set of correction factors corresponding to the second sample isoform, where the second set of correction factors is based on the reference standard.

The one or more processors can also be configured to determine, via the second MAM iteration and for the second time period, a second set of sample abundance values corresponding to the second sample isoform. The second set of sample abundance values can be based on the second set of correction factors. The MAM-based instrument, for the second time period, can have a second instrument condition defined by a second set of settings.

The second instrument condition of the MAM-based instrument for the first time period can be different from the second instrument condition of the MAM-based instrument for the second time period.

Based on the correction factors determined for each time period, variability of measurements can be reduced between the MAM iterations of the MAM-based instrument between the first time period and the second time period. For example, a variance value of the first set of sample abundance values and the second set of sample abundance values can be reduced based on the first set of correction factors of the first MAM-based instrument and the second set of correction factors of the second MAM-based instrument.

As further descried herein, for example, with respect to FIGS. 4a, 4b, 5a, and 5b, analysis of various isoforms demonstrates that application of the systems and methods disclosed herein reduce lab-to-lab and/or instrument-to-instrument variability (e.g., intermediate precision RSD) by two to three times when compared with existing MAM-based procedures. With the disclosed systems and methods, a consistent instrument model between labs, instruments, or between MAM iterations executed at different time periods, is no longer required. At the same time, small changes in digestion procedure between labs, as well as changes through automation, do not significantly affect assay results between different labs, instruments, or MAM iterations executed at different time periods.

The new system and methods also provide additional opportunities for other instrumentations, such as triple-quadrupole instrument for selected-reaction monitoring, because, with the disclosed systems and methods, consistent response factors between different peptide isoforms are no longer required.

In addition, disclosed systems and methods are significantly advantageous over conventional methods because the new systems and methods greatly reduce the lab-to-lab variation through run-time signal intensity calibration. The new system and methods, as described herein, effectively eliminate the requirement of MAM to use consistent equipment/instruments, which is a major problem in current MAM workflows. Moreover, the new systems and methods are applicable to any MAM-based application when accurate quantification of quality attributes is required. In addition, because reference standards are typically analyzed in parallel with samples in biopharmaceutical workflows, no additional work is needed for the analyst.

In accordance with the above, and with the disclosure herein, the present disclosure includes improvements in computer functionality or in improvements to other technologies at least because the claims recite that, e.g., MAM-based instrument(s) can be improved by reducing variability among MAM-based instruments running MAM procedures with the same sample (e.g., the same sample of proteolytic peptide(s)) and using a reference standard as a calibrant. That is, the present disclosure describes improvements in the functioning of the computer itself or any other technology or technical field because the systems and methods reduce variability across MAM-based instruments. This improves over the prior art at least because conventional MAM processes require conditions that are very difficult to meet because of variations of sample preparation procedure, analyst habit, instrument and reagent quality.

The present disclosure relates to improvement to other technologies or technical fields at least because MAM-based instruments can be calibrated even if they have different instrument models or have different sets of settings, even across different laboratories.

The present disclosure includes applying unique improvements with, or by use of, a particular machine, e.g., MAM-based instruments.

The present disclosure includes specific features other than what is well-understood, routine, conventional activity in the field of biotherapeutic development or research, and/or adds unconventional steps that focus the disclosure to particular useful applications, e.g., reducing lab-to-lab and instrument-to-instrument variability of multi-attribute method (MAM) via run-time signal intensity calibrations.

In addition, to overcome the challenges as described herein, new calibration systems and methods are described for calculation of attribute abundance in the sample, using the measured attribute in the reference standard as calibrant. In the reference standard, most quality attributes remain constant throughout the life of the standard and therefore can serve as calibrant to correct for difference between instruments or sample preparation procedures. Since reference standard data is usually collected in a typical MAM method, no additional work is needed from the analyst. Test data from a large number of attributes demonstrated that the methodology greatly reduces instrument-to-instrument variability. With this methodology, consistent instrument model and sample preparation procedure is no longer a requirement. As a result, changes in digestion procedure, advances of modern instrumentation will not significantly affect the assay result. The new systems and methods also allows for calibration of other instrumentations such as triple-quadrupole instrument for selected-reaction monitoring, because consistent response factors between different peptide isoforms are no longer a requirement.

As described herein, multi-attribute methods, based on proteolytic digestion followed by LC-MS analysis of proteolytic peptides, are developed to quantify a variety of quality attributes for therapeutic proteins. These methods take advantage of the resolving power provided by a mass spectrometric (MS) detector, and use the MS intensity of each isoform (including the modified and unmodified form) of a proteolytic peptide for quantitation. Due to the high specificity of these methods toward each clinically relevant quality attribute, such methods have gained substantial attention in the biopharmaceutical industry.

Advantages will become more apparent to those of ordinary skill in the art from the following description of the preferred embodiments which have been shown and described by way of illustration. As will be realized, the present embodiments can be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein:

FIG. 3 illustrates a method for reducing variability of a MAM-based instrument for multiple time periods via run-time signal intensity calibration in accordance with various embodiments disclosed herein.

The Figures depict preferred embodiments for purposes of illustration only. Alternative embodiments of the systems and methods illustrated herein can be employed without departing from the principles of the invention described herein.

DETAILED DESCRIPTION

Figure 1:
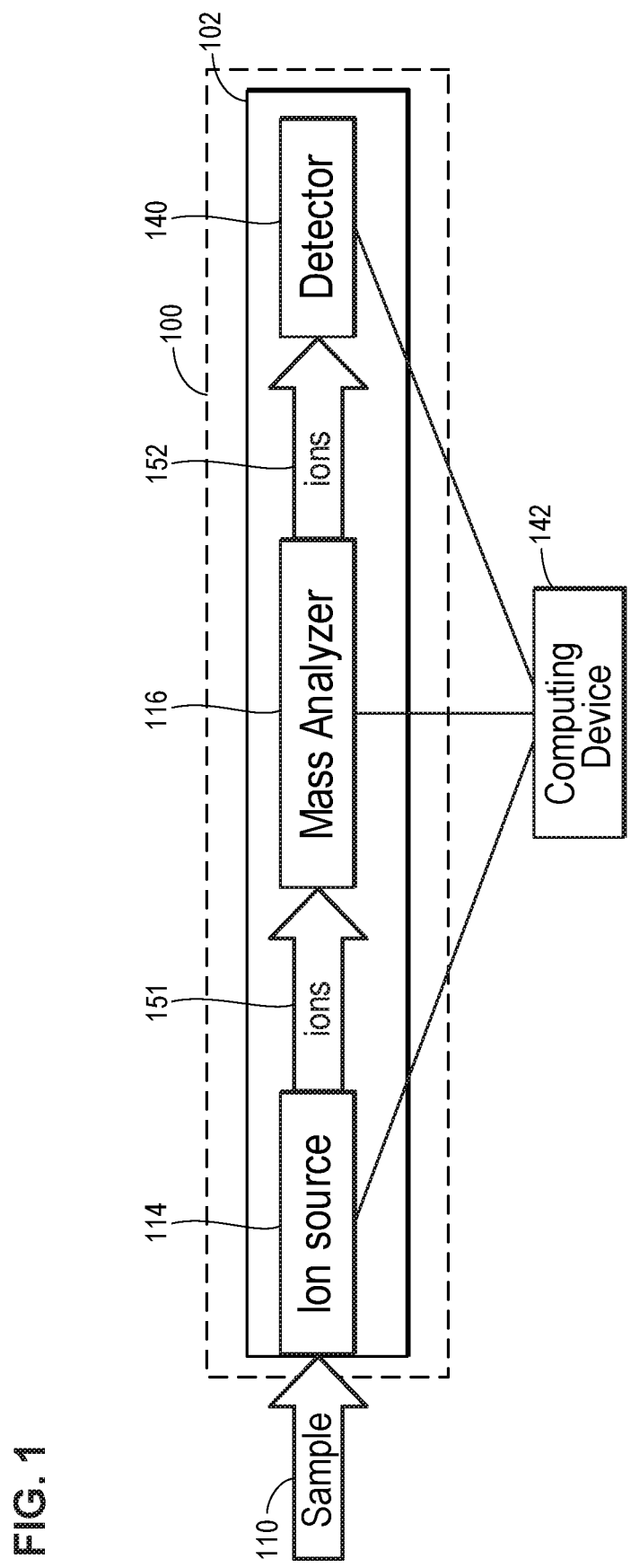
FIG. 1 illustrates an example MAM-based instrument including a mass spectrometer in accordance with various embodiments disclosed herein.

FIG. 1 illustrates an example MAM-based instrument 100 including a mass spectrometer (MS) 102 in accordance with various embodiments disclosed herein. As described herein, MAM can be used to analyze multiple properties or attributes (e.g., quality attributes) of a molecule (e.g., a protein or isoform) at once. In order to measure properties or attributes of individual molecules, mass spectrometer 102 can receive a sample 110 of molecules or peptides, such as a sample of isoforms or a reference standard of the isoform as described herein. The mass spectrometer 102 can convert the received sample of molecules into ions such that ionized forms of the sample molecules can be filtered and identified.

Generally, a mass spectrometer includes an ion source, a mass analyzer, and a detector. For example, for the ion source 114, a small sample (e.g., sample 110) of molecules or peptides is ionized (151), usually to cations by adding one or more protons. The mass analyzer 116 sorts and separates ions (e.g., ions 152) according to their mass and charge. The detector (e.g., detector 140) measures the separated ions, and the results can be recorded and displayed via computing device (e.g., computing device 142) having one or more processors, e.g., via a chart or other report. The one or more processors can be part of the MAM-based instrument 100 or part of a separate computing device (e.g., computing device 142).

Ions 152 can be detected electronically by detector 140, where the ions 152 have different intensities and, thereby, generate different or varying ion intensities (i.e., signals) that are detected by detector 140. The ions 152 detected by detector 140 can be read, stored, and/or analyzed in computing device 142, for example, where the detected ions can generate electronic information (e.g., peak areas of ion readings, etc.). Thus, as described herein, MAM-based instrument 100 can generate information regarding ion intensity. Ion intensity can be displayed via a two-dimensional (2D) chart, plot, or record, e.g., where the y-axis of a mass spectrum of such a chart can represent the signal intensity of the ions. Generally, a mass-to-charge (m/z) value is measured on the x-axis of the chart, plot, or record, where the "m" refers to the molecular or atomic mass number and the "z" refers to the charge number of the ion.

In addition, a response factor can be determined from analysis of ion intensity/signals generated from the MS information. The response factor can equal a ratio of an ion intensity signal produced by a molecule or isoform (e.g., as determined from ions 152) and a quantity of the molecule or isoform that produces the signal. Response factors (e.g., k) and ion intensities (e.g., $I_i$) are further described herein, for example, with respect to Table 1.

It is to be understood that ionization of molecules (e.g., isoforms) via a mass spectrometer can be accomplished in various ways. While the embodiment of the mass spectrometer of FIG. 1 is depicted and described in one such way, it is to be understood that any mass spectrometer, or method for performing mass spectrometry, can be used for the systems and methods described herein. For example, mass spectrometer 102 can include, or be based on, any of Orbitrap, TOF (time of flight), and/or single-, or triple-, quadrupole-based mass spectrometer instrumentation.

Computing device 142 can include one or more processors and or one or more computer memories for reading, storing, or analyzing molecular, isoform, reference standard, ion, or other information described herein. The one or more processors and/or one or more computer memories of computing device 142 can also be used to implement any of the functions, methods, flowcharts, or other features described herein with respect to reducing lab-to-lab or instrument-to-instrument variability of MAM analyses via run-time signal intensity calibration. In addition, or in the alternative, MAM-based instrument 100 can include one or more processors and/or one or more computer memories of computing device 142 that can also be used to implement any of the functions, methods, flowcharts, or other features described herein with respect to reducing lab-to-lab or instrument-to-instrument variability of MAM analyses via run-time signal intensity calibration, as described herein. As illustrated in FIG. 1, the computing device 142 can be commutatively coupled to the MAM-based instrument 100 directly (e.g., a hard-wired cable, such as a universal serial bus (USB) cable) or via a computer network (either private or public, such as via the Internet), and can be commutatively coupled to any of the components of mass spectrometer 102, including, for example, any of ion source 114, mass analyzer 116, and/or detector 140.

In particular, either MAM-based instrument 100 or computing device 142 can be a computing device that can include one or more processor(s) as well as one or more computer memories. The memories can include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memories can store an operating system (OS) (e.g., Microsoft Windows, Linux, Unix, etc.) capable of facilitating the functionalities as discussed herein. The memories can also store machine readable instructions, including any of one or more application(s), one or more software component(s), and/or one or more application programming interfaces (APIs), which can be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs can be, include, otherwise be part of, the machine learning component and/or the search engine optimization component, where each are configured to facilitate their various functionalities discussed herein. It should be appreciated that one or more other applications can be envisioned and that are executed by the processor(s) of MAM-based instrument 100 or computing device 142.

The processor(s) of MAM-based instrument 100 or computing device 142 can be connected to the memories of MAM-based instrument 100 or computing device 142 via a computer bus responsible for transmitting electronic data, data packets, or otherwise electronic signals to and from the processor(s) and memories in order to implement or perform the machine readable instructions, methods, processes, elements or limitations, as illustrated, depicted, or described for the various flowcharts, illustrations, diagrams, figures, and/or other disclosure herein.

The processor(s) of MAM-based instrument 100 or computing device 142 can interface with the memory via the computer bus to execute an operating system (OS). The processor(s) can also interface with the memory via the computer bus to create, read, update, delete, or otherwise access or interact with the data stored in the memories of MAM-based instrument 100 or computing device 142 and/or a database of MAM-based instrument 100 or computing device 142 (e.g., a relational database, such as Oracle, DB2, MySQL, or a NoSQL based database, such as MongoDB). The data stored in the memories and/or the database can include all or part of any of the data or information described herein, including, for example, the one or more search requests, the one or more transaction details, and the profile information of the user.

The MAM-based instrument 100 or computing device 142 can further include a communication component configured to communicate (e.g., send and receive) data via one or more external/network port(s) to one or more networks or local terminals, such as a computer network and/or computing device 142 described herein. In some embodiments, the communication component can include a client-server platform technology such as ASP.NET, Java J2EE, Ruby on Rails, Node.js, a web service or online API, responsive for receiving and responding to electronic requests. The processor(s) of MAM-based instrument 100 or computing device 142 can implement a communication component of MAM-based instrument 100 or computing device 142 that can interact to implement or perform the machine readable instructions, methods, processes, elements or limitations, as illustrated, depicted, or described for the various flowcharts, illustrations, diagrams, figures, and/or other disclosure herein. According to some embodiments, the communication component of MAM-based instrument 100 or computing device 142 can include, or interact with, one or more transceivers (e.g., WWAN, WLAN, and/or WPAN transceivers) functioning in accordance with IEEE standards, 3GPP standards, or other standards, and that can be used in receipt and transmission of data via external/network ports of MAM-based instrument 100 or computing device 142.

The MAM-based instrument 100 or computing device 142 can further include or implement an operator interface configured to present information to an administrator or operator and/or receive inputs from the administrator or operator. An operator interface of MAM-based instrument 100 or computing device 142 can provide a display screen (e.g., via computing device 142 106). Either of MAM-based instrument 100 or computing device 142 can also provide I/O components (e.g., ports, capacitive or resistive touch sensitive input panels, keys, buttons, lights, LEDs), which can be directly accessible via or attached to either of MAM-based instrument 100 or computing device 142 or can be indirectly accessible via or attached to a terminal of MAM-based instrument 100 or computing device 142. According to some embodiments, an administrator or operator can access the server 102 via the operator interface of MAM-based instrument 100 or computing device 142 and/or I/O components to review information, make changes, input training data, and/or perform other functions.

In some embodiments, either of MAM-based instrument 100 or computing device 142 can perform the functionalities as discussed herein as part of a "cloud" network or can otherwise communicate with other hardware or software components within the cloud to send, retrieve, or otherwise analyze data or information described herein.

In general, a computer program or computer-based product in accordance with some embodiments can include a computer usable storage medium, or tangible, non-transitory computer-readable medium (e.g., standard random access memory (RAM), an optical disc, a universal serial bus (USB) drive, or the like) having computer-readable program code or computer instructions embodied therein, wherein the computer-readable program code or computer instructions can be installed on or otherwise adapted to be executed by the processor(s) of MAM-based instrument 100 or computing device 142 (e.g., working in connection with the respective operating system in memories) to facilitate, implement, or perform the machine readable instructions, methods, processes, elements or limitations, as illustrated, depicted, or described for the various flowcharts, illustrations, diagrams, figures, and/or other disclosure herein. In this regard, the program code can be implemented in any desired program language, and can be implemented as machine code, assembly code, byte code, interpretable source code or the like (e.g., via Golang, Python, C, C++, C #, Objective-C, Java, Scala, Actionscript, Javascript, HTML, CSS, XML, etc.).

Figure 2:
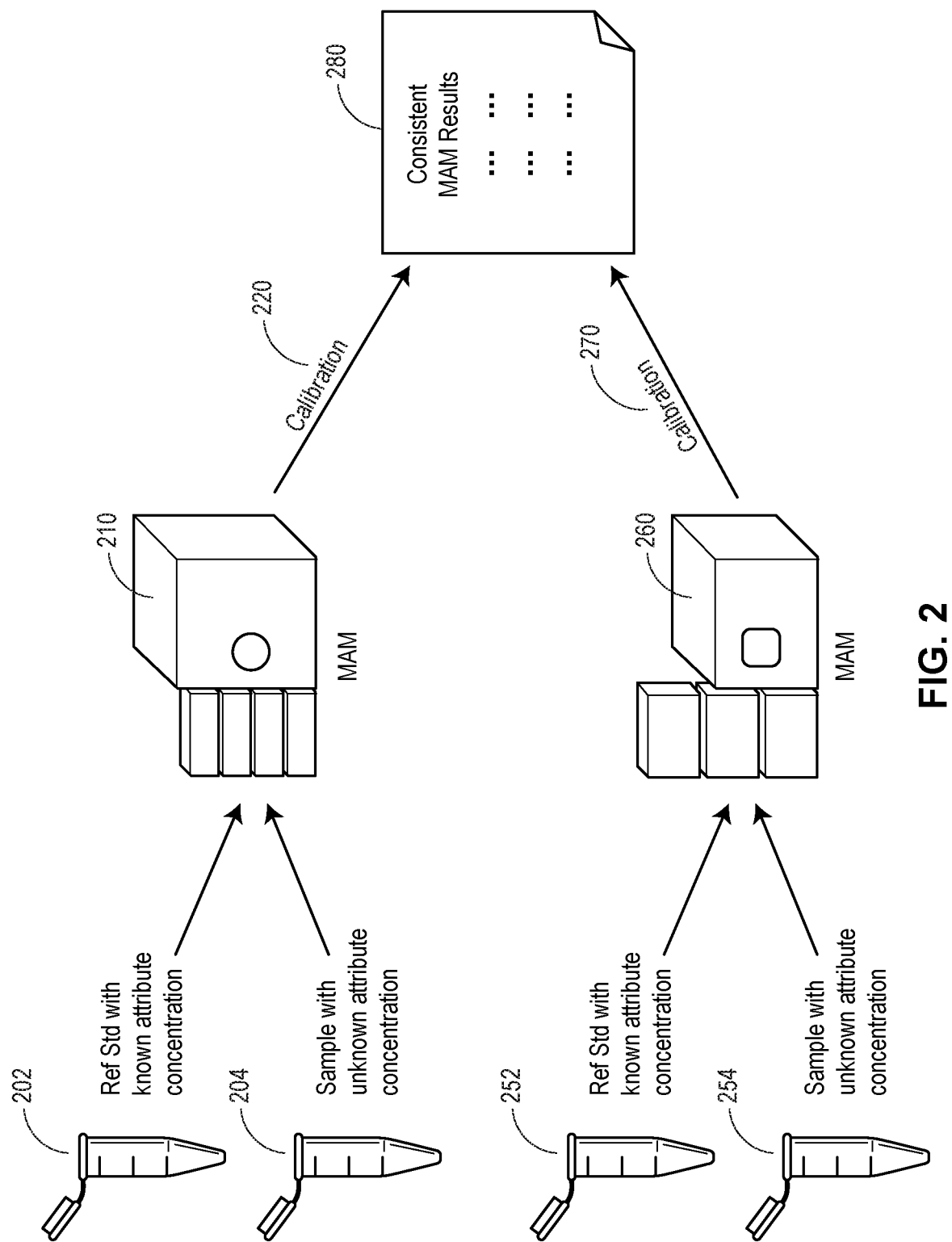
FIG. 2 illustrates an example flow diagram for reducing variability between a first MAM-based instrument and second MAM-based instrument via run-time signal intensity calibrations in accordance with various embodiments disclosed herein.

FIG. 2 illustrates an example flow diagram for reducing variability between a first MAM-based instrument 210 and second MAM-based instrument 260 via run-time signal intensity calibrations in accordance with various embodiments disclosed herein. In some embodiments, first MAM-based instrument 210 and second MAM-based instrument 260 can be located in a same laboratory. In other embodiments, first MAM-based instrument 210 and second MAM-based instrument 260 can be located in different labs. For example, first MAM-based instrument 210 can be situated at a first laboratory at a first geographical location and second MAM-based instrument 260 can be situated at a second laboratory at a second geographical location. In some embodiments, first MAM instrument 210 can be communicatively coupled to one or more processors associated with the second MS instrument via a computer network as described for FIG. 1.

Each of the first MAM-based instrument 210 and second MAM-based instrument 260 can be configured in the same or similar manner as described for MAM-based instrument 100 of FIG. 1. Accordingly, the disclosure for FIG. 1 applies in the same or similar fashion for either first MAM-based instrument 210 and/or second MAM-based instrument 260. In addition, each of first MAM-based instrument 210 and second MAM-based instrument 260 can include a computing device (e.g., computing device 142) as described for FIG. 1. In various embodiments, the first MAM-based instrument 210 and second MAM-based instrument 260 can be, or include, mass spectrometric (MS) instruments as described for FIG. 1. In other embodiments, the first MAM-based instrument 210 and second MAM-based instrument 260 can be, or include, triple-quadrupole instruments.

In the embodiment of FIG. 2, first MAM-based instrument 210 includes a first detector (e.g., detector 140 as described herein for FIG. 1). In addition, first MAM-based instrument 210 has a first instrument condition defined by (1) a first instrument model or (2) a first set of settings. For MAM-based instruments as described herein, an instrument model can define how the MAM-based instrument analyzes, reads, or otherwise reports molecules, isoforms, ions, or other related information as described herein. For example, an example embodiment instrument model, or configuration for ionizing molecules, is described herein for MAM-based instrument 100 of FIG. 1. Similarly, MAM-based instruments can include a set of settings of a MAM-based instrument can affect how the MAM-based instrument operates. For example, the settings can change how the MAM-based instrument performs ionization and/or change the sensitivity of how ions are read or detected or otherwise reported. A difference in either an instrument model or instrument settings can cause MAM-based instrument to operate in a different manner, which can cause the MAM-based instrument to detect and/or read molecules, isoforms, ions in a different manner. Thus, MAM-based instruments with different instrument models or instrument settings can have different conditions and may, therefore, operate differently from instrument-to-instrument and/or from lab-to-lab where such different instruments can be situated.

In the embodiment of FIG. 2, first MAM-based instrument 210 is configured to receive a first sample 204 (e.g., sample of a proteolytic peptide) and a reference standard 202 (e.g., of the proteolytic peptide). In the embodiment of FIG. 2, first sample 204 has an unknown attribute (e.g., a quality attribute) concentration. Reference standard 202, however, has a known attribute concentration and therefore can be used as a calibrant. For example, a reference standard can be a chemical sample that contains a certain known chemical composition, e.g., a sample with a certain lot number, or "lot," can contain 80% abundance of a first chemical or attribute, 10% of a second chemical or attribute, and various remaining percentages of other trace chemicals or attributes. The reference standard can have a same chemical or attribute composition and/or same signal signature (e.g., as detectable via a mass spectrometer as described for FIG. 1) as other reference standard samples of the same chemical or composition. Thus, the reference standard can be used for quality control purposes where a test sample (e.g., first sample 204 and/or second sample 254) is compared against the reference standard (e.g., reference standard 202 and/or reference standard 252) to determine the quality, quantity, consistency, variance, and/or deviation, between the test sample and the reference standard sample or lot. For example, the protein Epoetin alfa (recombinant erythropoietin) (e.g., Amgen's Epogen®) can have a reference standard lot that can be used to compare test sample lots of Epoetin for conducting quality control measures.

As shown for FIG. 2, for first MAM-based instrument 210, reference standard 202 is analyzed in parallel with sample 204. Similarly, for second MAM-based instrument 260, reference standard 252 is analyzed in parallel with second sample 254. For reference standards 202 and 252, most quality attributes remain constant throughout the life of each reference standard, and, therefore serve as a calibrant common to correct for difference(s) between instruments or sample preparation procedures, e.g., difference(s) in conditions between first MAM-based instrument 210 and second MAM-based instrument 260 and/or sample preparation procedures performed by lab analyst(s) operating first MAM-based instrument 210 and/or second MAM-based instrument 260.

As described herein, a benefit to using a reference standard as a calibrant in each run (e.g., where reference standards 202 and 252 can be samples of the same reference standard used as a calibrant), is that most requirements for conventional MAM regarding lab-to-lab and instrument-to-instrument reproducibility can be eliminated. For example, assumptions as to lab-to-lab and instrument-to-instrument reproducibility can be simplified and revised as follows: (1) unmodified and modified peptides have reproducible recovery in the same LC/MS sequence (e.g., compared to between labs); (2) unmodified and modified peptides have reproducible MS response factor in the same LC/MS sequence (e.g., compared to the same response factor); (3) artificially induced attribute changes are negligible. These above requirements are easier to meet than compared to conventional method requirements, because most requirements regarding lab-to-lab reproducibility are reduced to the reproducibility within the same LC/MS sequence (e.g., same lab, same analyst, and same day).

As shown in the embodiment of FIG. 2, first MAM-based instrument 210 is configured, via its first detector, to detect a first sample isoform from the first sample and a first reference standard isoform from the reference standard. In the context of proteolytic peptides, a protein-based isoform can be a protein variant that is a member of a set of highly similar proteins that perform the same or similar biological roles. In some embodiments, the first sample isoform can be a quality attribute used for quality control purposes as described herein. In other embodiments, the quality attribute can be a protein or identified impurity other measure for determining quality of a sample or lot. For example, in various embodiments, the quality attribute can be defined by fragmentation, oxidation, glycation, hydroxylation, sequence variants, isomerization, deamination, C-terminal lysine, O-linked glycans, and/or N-linked glycans.

First MAM-based instrument 210 can be associated with one or more processors. The one or more processors can be included with first MAM-based instrument 210 or can be part a computing device (e.g., computing device 142) commutatively coupled to first MAM-based instrument 210 as described, for example, for FIG. 1.

In the embodiment of FIG. 2, the one or more processors associated with the first MAM-based instrument 210 are configured to determine, via a first MAM iteration, a first set of correction factors corresponding to the first sample isoform. It is to be understood that the determination of the set of correction factors can be made before, during, or after the first MAM iteration such that the determination of the set of correction factors is associated with the first MAM iteration. It is to be further understood that the set of correction factors, as described herein, can include a single correction factor or multiple correction factors. In the embodiment of FIG. 2, the first set of correction factors is based on reference standard 202. This relationship can be expressed via the following equation (1) for n+1 isoforms associated with a particular amino acid residue, where $a_i$ represents the first set of correction factors and/° and A° represent ion intensity and attribute abundance values of reference standard 202.

$$\begin{cases} a_i = \dfrac{I_i^0}{I_0^0} \dfrac{A_0^0}{A_i^0}, \; i = 0, n \\ A_i = \dfrac{I_i/a_i}{\sum_{j=0}^{n} \dfrac{I_j}{a_j}}, \; i = 0, n \end{cases} \quad (1)$$

Thus, the reference standard (e.g., represented via $I^0$ and $A^0$) is used as a calibrant where the first set of correction factors (e.g., $a_i$) is determined from such values. As shown for equation (1), the first set of correction factors (e.g., $a_i$) is based on ion intensity values (e.g., $I_0^0$ and $I_i^0$) of the first reference standard isoform(s) and first reference standard abundance values (e.g., $A_0^0$ and $A_i^0$) of the first reference standard isoform(s). Table 1 below describes various notations used for equation (1), and/or as used elsewhere herein:

TABLE 1

| Notation | Description |
| --- | --- |
| Superscript 0 | Values having superscript 0 represent values of the reference standard (e.g., reference standard samples 202 or 252) |
| $A^0$ | Represents the known abundance of an isoform in a reference standard (e.g., reference standard samples 202 or 252) |
| $I^0$ | Represents the measured ion intensity of a reference standard (e.g., reference standard samples 202 or 252) |
| Subscripts 0, 1, 2, . . . i, . . . n | Subscript 0, 1, 2, . . . i, . . . n represent the n + 1 isoforms on a specified residue (including the unmodified form). Subscript 0 represents the most abundant form in a reference standard (e.g., reference standard samples 202 or 252), which is usually the unmodified form |
| $k_i$ | Represents the response factor of isoform i |
| $a_i$ | Represents the correction factor (e.g., the response factor correction factor) for isoform i |
| $a_0$ | The value of $a_0$ is defined as 1 |
| $A_i$ | Represents the abundance of isoform i |
| $I_i$ | Represents the ion intensity (peak area) of isoform i |

Equation (1) can be used to perform intensity calibration (e.g., ion intensity calibration) based on known attribute abundance in the reference standard ($A_i^0$).

In addition, the first set of correction factors (e.g., $a_i$) can be used to calibrate a response factor (k) associated with the first set of sample abundance values (e.g., $A_i$) to determine the ion intensity value(s) ($I_i$) of the first sample isoform(s). This is shown in equation (2) below. In general, ion intensity values can represent peak areas as detected by the MS detector 140 as describe for FIG. 1. As shown below, correction factor $a_i$, can be used to calibrate a response factor k, that when applied to an abundance value ($A_i$) causes calibration of ion intensity factor $I_i$. This is shown in equation (2) below, from which equation (1) is derived:

$$\begin{cases} a_i k^0 A_i^0 = I_i^0, \; i = 0, n \\ a_i k A_i = I_i, \; i = 0, n \\ a_0 = 1 \\ \sum_{j=0}^{n} A_j = 1 \end{cases} \quad (2)$$

In equation (2), response factor (k) for each isoform (i) is modified by correction factor ($a_i$). The formula $a_i k^0$ represents the corrected response factor for the reference standard (e.g., 202) and the $a_i k$ represents the corrected response factor for the sample (e.g., first sample 204). The response factor for the reference standard ($k^0$) can be different from the response factor of first sample 204 (k) due to slight differences in sample preparation, as well as differences in instrument sensitivity between injections (e.g., within-lab variation). Similarly, differences can be similarly introduced or occur between first sample 204 and second sample 254 (e.g., lab-to-lab variation). As shown in equation (2), in some embodiments, a correction a factor $a_0$ is set to 1 ($a_0=1$) to solve equation (2) to derive equation (1). However, it is to be understood that it is not important which isoform is set to a constant value ($a_0$=1); however, generally the most abundant isoform is set, which is usually the unmodified isoform.

The abundance value ($A_i^o$) of each attribute in a reference standard can be either established using a conventional MAM method or an orthogonal method with better accuracy. If an absolute quantitation method is used, all subsequent MAM analyses of the same attribute become an absolute measurement after calibration.

Equations (1) and (2) can be used to calculate an abundance value ($A_i$) of each isoform i in a sample (e.g., first sample 204). For example, as shown for equation (1), the abundance value ($A_i$) of isoform i is determined from values including the correction factor (e.g., $a_i$) and signal intensity of each isoform (e.g., isoform $I_i$).

In the embodiment of FIG. 2, the one or more processors associated with first MAM-based instrument 210 can further be configured to determine a first set of sample abundance values (e.g., Ai as shown for equation (1)) corresponding to the first sample isoform(s), where the first set of sample abundance values (e.g., $A_i$ as shown for equation (1)) is based on the first set of correction factors (e.g., $a_i$ of equation (1)). As described herein, abundance values can be reported as a percentage. As shown for equation (1), the first set of sample abundance values (e.g., $A_i$) is further based on ion intensity value(s) of the first sample isoform(s) (e.g., $I_i$ of equation (1)).

FIG. 2 also illustrates calibration of a second MAM-based instrument 260. Second MAM-based instrument 260 is calibrated (270) using the same reference standard (or different sample of the same reference standard) as used to calibrate (220) the first MAM-based instrument 210. In this manner, both second MAM-based instrument 260 and first MAM-based instrument 210 achieve consistent results as can be shown via report 280. It is to be understood that the second MAM-based instrument 260 is configured and calibrated in the same or similar manner as described for first MAM-based instrument 210, including use of the same reference standard (e.g., where reference standard 202 and reference standard 252 are samples of the same reference standard) such that the disclosure herein for calibration (e.g., including via equations (1) and (2)), apply equally for second MAM-based instrument 260 as for first MAM-based instrument 210.

Second MAM-based instrument 260 includes a second detector (e.g., detector 140 as described herein for FIG. 1). In the embodiment of FIG. 2, second MAM-based instrument 260 has a second instrument condition defined by at least one of: (1) a second instrument model or (2) a second set of settings. As described herein, the second instrument condition of second MAM-based instrument 260 can be different from the first instrument condition of first MAM-based instrument 210. In some embodiments, the second instrument condition can differ from the first instrument condition because the second MAM-based instrument 260 can have a second instrument model that differs from the first instrument model of the first MAM-based instrument 210. In other embodiments, the second instrument condition can differ from the first instrument condition because the second MAM-based instrument 260 can have a second set of settings that differs from a first set of settings of the first MAM-based instrument 210.

Second MAM-based instrument 260 is configured to receive a second sample 254 (e.g., sample of a proteolytic peptide) and the reference standard 252 (e.g., of the proteolytic peptide). Reference standard 252 can be a different sample of the same reference standard as used for reference standard 202. The second MAM-based instrument 260 is further configured to, via the second detector (e.g., detector 140 as described herein for FIG. 1), detect a second sample isoform (i) from the second sample and a second reference standard isoform from the reference standard. It is to be appreciated that, in some embodiments, each of the first sample, second sample, and reference may be associated with a common proteolytic peptide such that the first sample is of a given proteolytic peptide, the second sample of the proteolytic peptide, and the reference standard is of the proteolytic peptide.

Second MAM-based instrument 260 is associated with one or more processors. In some embodiments the one or more processors are part of a same computing device (e.g., computing device 142) such that the one or more processors associated with the first MAM-based instrument 210 are the same one or more processors associated with second MAM-based instrument 260. In other embodiments, the one or more processors are part of different computing devices.

The one or more processors associated with second MAM-based instrument 260 are configured to determine, via a second MAM iteration, a second set of correction factors (e.g., $a_i$) corresponding to the second sample isoform(s) (i). It is to be understood that the determination of the set of correction factors (e.g., $a_i$) can be made before, during, or after the second MAM iteration such that the determination of the set of correction factors is associated with the second MAM iteration. In the embodiment of FIG. 2, the second set of correction factors (e.g., $a_i$) is based on reference standard 252, which is a same reference standard as that of reference standard 202. The one or more processors associated with the second MAM-based instrument 260 are further configured to determine a second set of sample abundance values (e.g., $A_i$) corresponding to the second sample isoform(s), where the second set of sample abundance values (e.g., $A_i$) is based on the second set of correction factors (e.g., $a_i$).

Based on the correction factors determined for each of first MAM-based instrument 210 and second MAM-based instrument 260, as calibrated by the common reference standards 202 and 252 described herein, variability of measurements can be reduced between the first MAM-based instrument 210 and second MAM-based instrument 260, when the same sample is analyzed by both instruments. The reduced variability can be demonstrated via consistent MAM results of report 280. For example, variance value(s) determined from the first set of sample abundance values (e.g., $A_i$) of and the second set of sample abundance values (e.g., $A_i$) can be reduced based on applying the first set of correction factors (e.g., $a_i$) of first MAM-based instrument 210 and the second set of correction factors (e.g., $a_i$) of second MAM-based instrument 260 as described herein. As described herein, in some cases, the variance value of the first set of sample abundance values and the second set of sample abundance values may be reduced by at least 25 percent.

Thus, as illustrated for FIG. 2, samples 204 and 254 and a common reference standard (e.g., 202 and 252) can be analyzed in parallel for calibration (220 and 270) of first MAM-based instrument 210 and second MAM-based instrument 260, respectively. In this manner, a report 280 reporting the concentration of each quality attribute in the sample can be generated using known concentration in the reference standard (e.g., 202 and 252), to achieve consistent results even with different instrumentation, e.g., instrumentation having different conditions as described herein. For example, each of first MAM-based instrument 210 and first MAM-based instrument 216 can be configured to generate a report (e.g., report 280) including, or otherwise describing or reporting, the isoforms and/or quality attribute(s). For example, the report 280 can include the information or data reported as a chart, and can include data or information such as response factors, peak areas, or other information, for example, as described for FIG. 1. In various embodiments, report 280 can be generated after calibration (220 or 270) using the reference standard 202 or 252 as described herein.

FIG. 3 illustrates a method 300 for reducing variability of a MAM-based instrument (e.g., MAM-based instrument 100) for multiple time periods via run-time signal intensity calibration in accordance with various embodiments disclosed herein. It is to be understood that the MAM-based instrument of FIG. 3 is configured and calibrated in the same or similar manner as described for first MAM-based instrument 210 of FIG. 2, including use of a reference standard such that the disclosure herein for calibration (e.g., including via equations (1) and (2)), apply equally for the MAM-based instrument of FIG. 3. With respect to FIG. 3, however, the same MAM-based instrument is used across different time periods (e.g., across different runs, different MAM iterations, and/or different days, hours, etc.). The MAM-based instrument of FIG. 3 can be configured as described for MAM-based instrument 100 of FIG. 1.

Method 300 begins (302) at block 304, where the MAM-based instrument of FIG. 3, for a first time period, can receive a first sample (e.g., sample 204, which may be of a proteolytic peptide) and a reference standard (e.g., reference standard 202, which may be of the proteolytic peptide).

At block 306, the MAM-based instrument can detect, via a detector (e.g., detector 140) for the first time period, a first sample isoform (i) from the first sample and a first reference standard isoform from the reference standard.

At block 308, one or more processors (e.g., one or more processors as described for FIG. 1) can be configured to, via a first MAM iteration for the first time period, determine a first set of correction factors (e.g., $a_i$) corresponding to the first sample isoform(s) (i), where the first set of correction factors (e.g., $a_i$) is based on the reference standard.

At block 310, the one or more processors can also be configured to determine, via the first MAM iteration and for the first time period, a first set of sample abundance values (e.g., $A_i$) corresponding to the first sample isoform(s) (i). The first set of sample abundance values can be based on the first set of correction factors (e.g., $a_i$). The MAM-based instrument, for the first time period, can have a first instrument condition defined by a first set of settings. The first instrument condition can be the same or similar as described for FIG. 2.

At block 312, the MAM-based instrument, for a second time period, can receive a second sample (e.g., which may be of a proteolytic peptide) and the reference standard (e.g., which may be of the proteolytic peptide).

At block 314, the MAM-based instrument can detect, via the detector (e.g., detector 140) for the second time period, a second sample isoform (i) from a second sample and a second reference standard isoform from the reference standard.

At block 316, the one or more processors can be configured to, via a second MAM iteration for the second time period, determine a second set of correction factors corresponding to the second sample isoform(s), where the second set of correction factors is based on the reference standard.

At block 318, the one or more processors can also be configured to determine, via the second MAM iteration and for the second time period, a second set of sample abundance values corresponding to the second sample isoform(s). The second set of sample abundance values can be based on the second set of correction factors. The MAM-based instrument, for the second time period, can have a second instrument condition defined by a second set of settings. The second instrument condition of the MAM-based instrument for the first time period can be different from the second instrument condition of the MAM-based instrument for the second time period.

Based on the correction factors determined for each time period, variability of measurements can be reduced between the MAM iterations for the first time period and the second time period. For example, the variance value(s) of the first set of sample abundance values and the second set of sample abundance values can be reduced based on the first set of correction factors of the first MAM-based instrument and the second set of correction factors of the second MAM-based instrument.

Figure 4A:
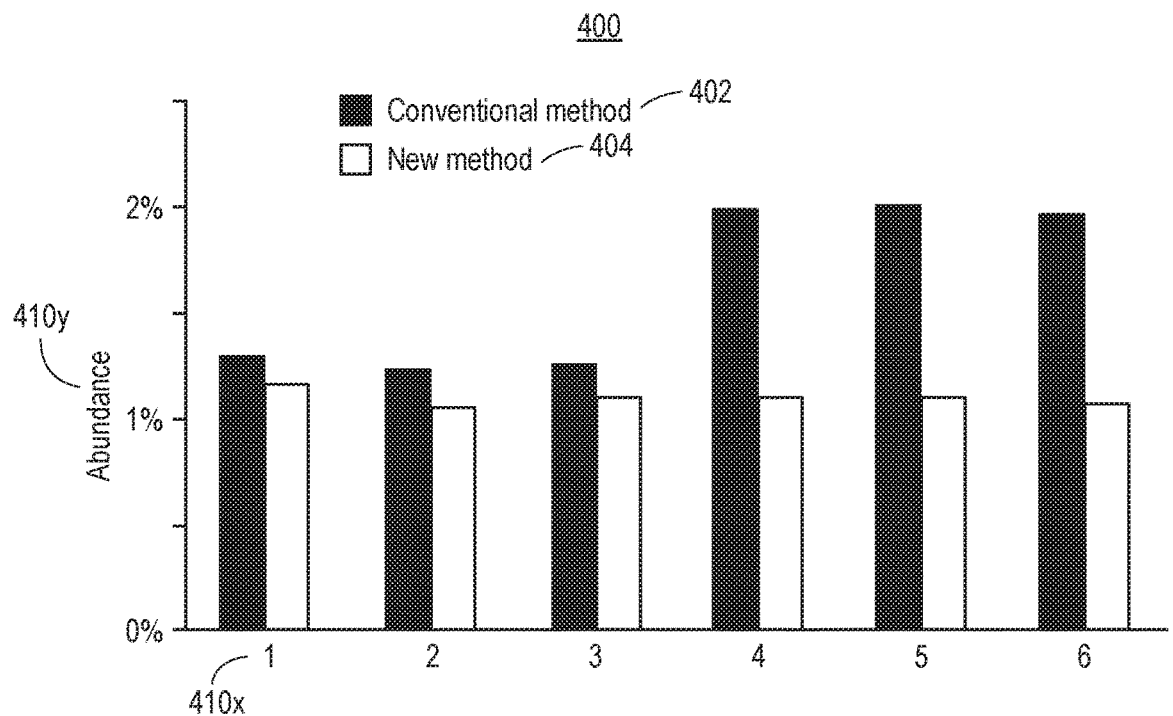
FIG. 4a illustrates a diagram depicting a reduction in instrument-to-instrument/lab-to-lab variance of abundance values for a given isoform across six example MAM iterations in accordance with various embodiments disclosed herein.
Figure 4B:
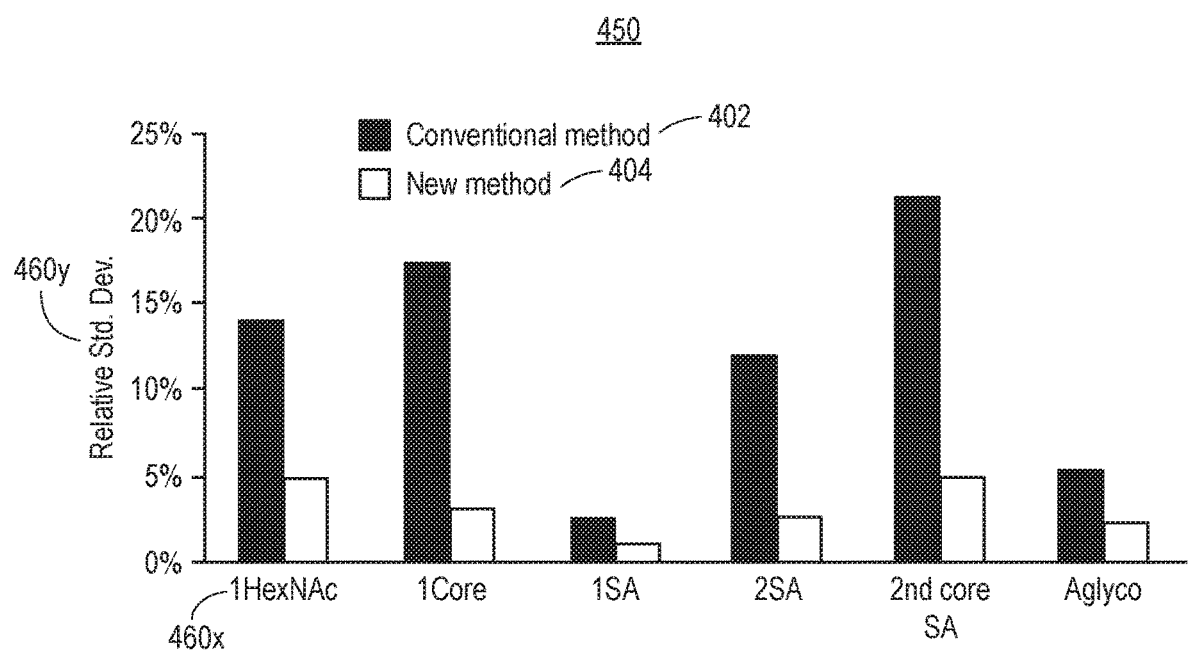
FIG. 4b illustrates a diagram depicting a reduction in instrument-to-instrument/lab-to-lab deviations for six example isoforms, including the isoform of FIG. 4a, in accordance with various embodiments disclosed herein.

The embodiments of FIGS. 4a and 4b, as described herein, illustrate an analysis of a protein, P1, using variance reduction and calibration as disclosed herein. P1 contains two O-linked glycosylation sites in one portion of the molecule, with 6 different glycoforms (isoforms), each as shown in FIG. 4b herein. Diagrams 400 and 450 of FIGS. 4a and 4b, respectively, were generated by analyzing a P1 sample, together with its reference standard, by different lab analysts using different LC/MS instruments, including a Q Exactive™ BioPharma Platform instrument and two Exactive™ Plus Orbitrap Mass Spectrometer instruments, each manufactured by the ThermoFisher Scientific company (San Jose, Calif.). All data was processed on Chromeleon™ software, provided by the ThermoFisher Scientific company, to determine peak area(s) of each peptide of interest. The abundance values (e.g., $A_i$) illustrated for each glycoform of FIGS. 4a and 4b were quantified using conventional MAM iterations (402) as well as new calibrated MAM iterations (404). The new calibrated MAM procedures (404) are based on calibration techniques for reducing lab-to-lab or instrument-to-instrument variability of Multi-Attribute Methods (MAM) via run-time signal intensity calibration as described herein. To obtain the abundance values (e.g., $A_i^0$) of each attribute in the P1 reference standard, the P1 reference standard was analyzed by conventional MAM iterations (402) six times, and the average value of the six measurements was used as the known abundance in the reference standard.

FIG. 4a illustrates a diagram 400 depicting a reduction in instrument-to-instrument/lab-to-lab variance of abundance values (e.g., $A_i$) for a given isoform across six example MAM iterations. For example, the y-axis 410y of diagram 400 shows abundance values (e.g., $A_i$) as percentages. The x-axis 410x of diagram 400 shows six example MAM iterations 1-6 that compare conventional sample abundance values determined using conventional MAM iterations (402) against calibrated abundance values determined using new calibrated MAM iterations (404) as described for various embodiments disclosed herein. For example, MAM iterations 1-6 can be MAM iterations ran on different MAM-instruments (e.g., first MAM-instrument 210 and second MAM-based instrument 260 as described for FIG. 2) or MAM iterations 1-6 can be MAM iterations ran across different time periods on the same MAM-instrument (e.g., as described for FIG. 3).

Specifically, in the embodiment of FIG. 4a, diagram 400 shows measured abundance values (e.g., $A_i$) for a glycoform (an isoform) as determined using both conventional MAM iterations (402) and new calibrated MAM iterations (404).

In particular, the glycoform of diagram 400 is 2nd-core sialic acid (SA). Iterations 1-3 shown on x-axis 410x were measured on a first MAM-based instrument, i.e., a first Exactive™ Plus Orbitrap Mass Spectrometer instrument. Iterations 4-6 shown on x-axis 410x were measured on a different, second MAM-based instrument, i.e., a different Exactive™ Plus Orbitrap Mass Spectrometer instrument. As shown in diagram 400, the instrument-to-instrument variability of abundance values (e.g., $A_i$) across each iteration 1-6 using the new calibrated MAM procedures (404) is significantly reduced compared with the variability of abundance values across each iteration 1-6 using conventional MAM procedures (402). Said another way, the instrument-to-instrument consistency of abundance values (e.g., $A_i$) across each iteration 1-6 using the new calibrated MAM procedures (404) is significantly enhanced compared with the variability of abundance values across each iteration 1-6 using conventional MAM procedures (402).

FIG. 4b illustrates a diagram depicting a reduction in instrument-to-instrument/lab-to-lab deviations for six example isoforms, including the isoform of FIG. 4a, in accordance with various embodiments disclosed herein. The y-axis 460y of diagram 450 shows intermediate precision relative standard deviation (RSD) as a percentage. RSD is correlated with abundance values (e.g., $A_i$). In particular, a reduction in RSD shows a reduction in variability of abundance values.

The x-axis 460x of diagram 400 shows the six example isoforms (1HexNAc, 1Core, 1SA, 2SA, 2nd-core SA, and Aglyco). Analysis for the 2nd-core SA isoform is shown for FIG. 4a as described herein. FIG. 4b shows a percentage reduction in relative standard deviation (RSD) (e.g., glycoforms) across each of the six isoforms, as shown when conventional MAM iterations (402) are compared against new calibrated MAM iterations (404). Each of the six isoforms can be used as quality attributes to test for quality control of lots of a given sample (e.g., P1). Hence, consistency (i.e., reduced variability/deviation) across measurements of the same sample is important. As shown by diagram 450 of FIG. 4b, the new calibrated MAM iterations (404) decrease the RSD by a significant amount (e.g., two to three times), from a maximum of 25% to a maximum of 5%, even when the P1 glycoforms were measured across different instruments.

Figure 5A:
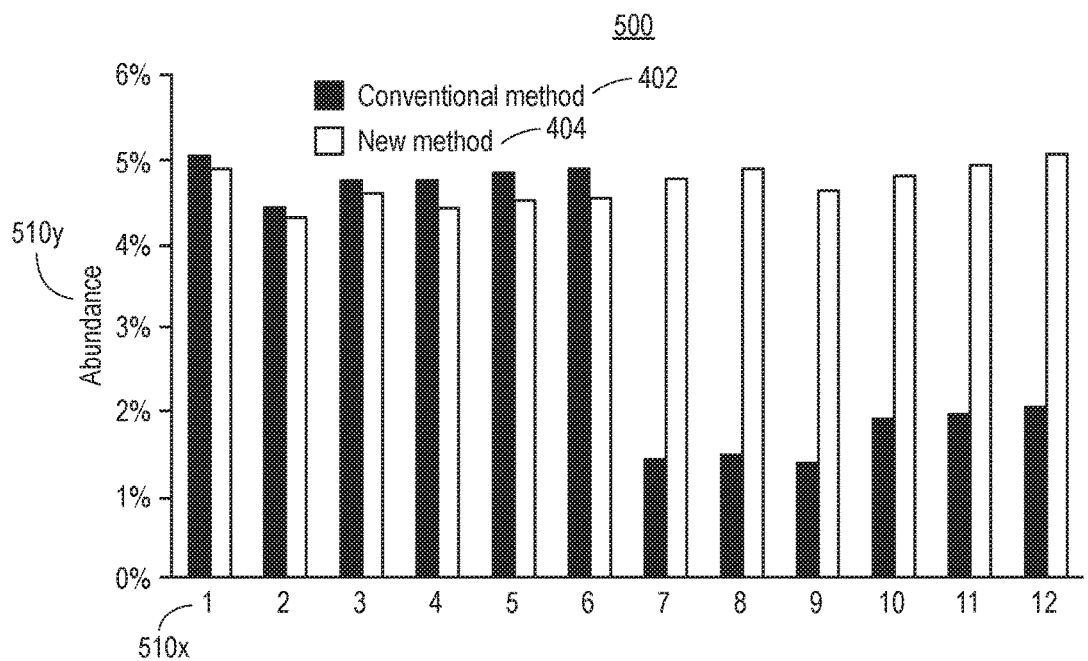
FIG. 5a illustrates a diagram depicting a reduction in instrument-to-instrument/lab-to-lab variance of abundance values across twelve example MAM iterations in accordance with various embodiments disclosed herein.
Figure 5B:
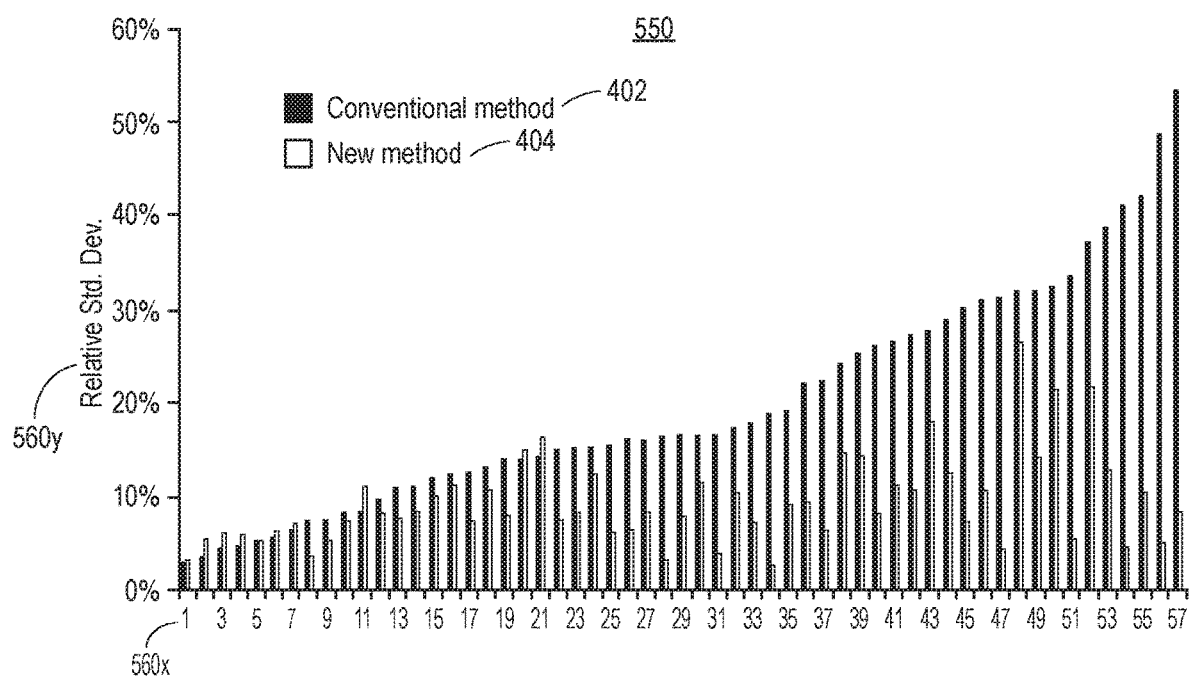
FIG. 5b illustrates a diagram depicting a reduction in instrument-to-instrument/lab-to-lab deviations across 57 quality attributes in accordance with various embodiments disclosed herein.

The embodiments of FIGS. 5a and 5b, as described herein, illustrate an analysis of attributes a second protein, P2. In particular, with respect to diagrams 500 and 550 of FIGS. 5a and 5b, a P2 reference standard was incubated at 40° C. for 4 weeks. Then 20% of this stressed sample was spiked into the P2 reference standard to create a test sample. This test sample, together with both the P2 reference standard as well as the stressed sample, was digested with trypsin with two different protocols, and each digest was analyzed three times on two different LC/MS instrument with different columns, mobile phase and gradient. A Thermo Q Exactive™ BioPharma Platform instrument was used as a first MAM-based instrument and an Orbitrap Fusion™ Lumos™ Tribrid™ Mass Spectrometer (ThermoFisher Scientific) as a second-MAM based instrument. The P2 reference standard was analyzed on the first MAM-based instrument six times and the average measured abundance value of each attribute was used as a standard abundance value. All resulting data and information was analyzed to obtain peak areas of each peptide isoform and related abundance values.

In addition, with respect to FIGS. 5a and 5b, 57 quality attributes of P2 were analyzed. For example, the 57 quality attributes include fragmentation, oxidation, glycation, hydroxylation, sequence variants, isomerization, deamidation, C-terminal lysine, O-linked glycans and N-linked glycans. The quality attributes covered a wide range of abundance values from 0.005% to 5%.

FIG. 5a illustrates diagram 500 depicting a reduction in instrument-to-instrument/lab-to-lab variance of abundance values (e.g., $A_i$) across twelve example MAM iterations. For example, the y-axis 510y of diagram 500 shows abundance values (e.g., $A_i$) as percentages. The x-axis 510x of diagram 500 shows twelve example MAM iterations 1-12 that compare conventional sample abundance values determined using conventional MAM iterations (402) against calibrated abundance values determined using new calibrated MAM iterations (404) as described for various embodiments disclosed herein. For example, MAM iterations 1-12 can be MAM iterations performed using different instruments (e.g., first MAM-instrument 210 and second MAM-based instrument 260 as described for FIG. 2) or MAM iterations 1-12 can be MAM iterations performed using different time periods on the same MAM-instrument (e.g., as described for FIG. 3).

Specifically, in the embodiment of FIG. 5a, diagram 500 shows measured abundance values (e.g., $A_i$) for K117 hydroxylation as determined using both conventional MAM iterations (402) and new calibrated MAM iterations (404). In particular, diagram 500 illustrates measured abundance of K117 hydroxylation by two digestion protocols and two LC/MS instruments, each in triplicate. MAM iterations 1-3 and 7-9 are from digestion protocol 1 and runs 4-6 and 10-12 are from digestion protocol 2. MAM iterations 1-6 are executed on a Thermo Q Exactive™ BioPharma Platform instrument, and MAM iterations 7-12 are executed on an Orbitrap Fusion™ Lumos™ Tribrid™ Mass Spectrometer. As shown in diagram 500, the instrument-to-instrument variability of abundance values (e.g., $A_i$) across all MAM iterations 1-12 using the new calibrated MAM procedures (404) is significantly reduced compared with the variability of abundance values across the MAM iterations 1-12 using conventional MAM procedures (402). Said another way, the instrument-to-instrument consistency of abundance values (e.g., $A_i$) across each MAM iteration 1-12 using the new calibrated MAM procedures (404) is significantly enhanced compared with the variability of abundance values across each MAM iteration 1-12 using conventional MAM procedures (402). Thus, FIG. 5a illustrates measured abundance values of K117 hydroxylation for two different instrument models. With the conventional MAM procedure (402), different abundance variations were obtained across the two different MAM-based instruments. However, the new calibrated MAM procedures (404) provided consistent abundance values across the two different MAM-based instruments.

FIG. 5b illustrates a diagram depicting a reduction in instrument-to-instrument/lab-to-lab deviations across 57 quality attributes in accordance with various embodiments disclosed herein. The K117 hydroxylation of FIG. 5a accounts for one of the 57 quality attributes of FIG. 5b. The y-axis 560y of diagram 550 shows intermediate precision RSD as a percentage. The x-axis 560x of diagram 550 shows the 57 quality attributes, of which K117 hydroxylation is one such quality attribute. Each of the 57 quality attributes was determined using conventional MAM procedure (402) and the new calibrated MAM procedure (404). Diagram 550 of FIG. 5b shows that while the RSD of the quality attributes using the conventional MAM procedure (402) were generally in the range of 3-50%, the RSD of the quality attributes using the new calibrated MAM procedures (404) were reduced to less than 20% for most quality attributes, thus showing a reduction in variability via run-time signal intensity calibrations in accordance with various embodiments disclosed herein.

As described herein, reducing variability of a MAM-based instrument(s) via run-time signal intensity calibration yields advantages for mass spectrometry (e.g., as described for FIG. 2). For example, calibrating response factors (e.g., $a_i$), as described herein, eliminates the requirement of different peptide isoforms having to have the same response factor (k). This technique can be applied to other types of instrumentation for MAM purposes. For example, with respect to conventional methodologies, selected-reaction monitoring (SRM) on a triple-quadrupole instrument does not work for MAM purposes due to potentially different fragmentation efficiencies among peptide isoforms. The new calibrated MAM procedure described herein, however, makes it possible to perform MAM on a triple-quadrupole instrument, which can be more advantageous than using an orbitrap instrument due to triple-quadrupole instrument's better precision, linearity and dynamic range. In such embodiments, the concentration of each attribute in the reference standard, however, may need to be established initially on a high-resolution instrument.

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments can be implemented, using either current technology or technology developed after the filing date of this patent, which would still fall within the scope of the claims.

The following additional considerations apply to the foregoing discussion. Throughout this specification, plural instances can implement components, operations, or structures described as a single instance. Although individual operations of one or more methods are illustrated and described as separate operations, one or more of the individual operations can be performed concurrently, and nothing requires that the operations be performed in the order illustrated. Structures and functionality presented as separate components in example configurations can be implemented as a combined structure or component. Similarly, structures and functionality presented as a single component can be implemented as separate components. These and other variations, modifications, additions, and improvements fall within the scope of the subject matter herein.

Additionally, certain embodiments are described herein as including logic or a number of routines, subroutines, applications, or instructions. These can constitute either software (e.g., code embodied on a machine-readable medium or in a transmission signal) or hardware. In hardware, the routines, etc., are tangible units capable of performing certain operations and can be configured or arranged in a certain manner In example embodiments, one or more computer systems (e.g., a standalone, client or server computer system) or one or more hardware modules of a computer system (e.g., a processor or a group of processors) can be configured by software (e.g., an application or application portion) as a hardware module that operates to perform certain operations as described herein.

The various operations of example methods described herein can be performed, at least partially, by one or more processors that are temporarily configured (e.g., by software) or permanently configured to perform the relevant operations. Whether temporarily or permanently configured, such processors can constitute processor-implemented modules that operate to perform one or more operations or functions. The modules referred to herein may, in some example embodiments, comprise processor-implemented modules.

Similarly, the methods or routines described herein can be at least partially processor-implemented. For example, at least some of the operations of a method can be performed by one or more processors or processor-implemented hardware modules. The performance of certain of the operations can be distributed among the one or more processors, not only residing within a single machine, but deployed across a number of machines. In some example embodiments, the processor or processors can be located in a single location, while in other embodiments the processors can be distributed across a number of locations.

The performance of certain of the operations can be distributed among the one or more processors, not only residing within a single machine, but deployed across a number of machines. In some example embodiments, the one or more processors or processor-implemented modules can be located in a single geographic location (e.g., within a home environment, an office environment, or a server farm). In other embodiments, the one or more processors or processor-implemented modules can be distributed across a number of geographic locations.

This detailed description is to be construed as exemplary only and does not describe every possible embodiment, as describing every possible embodiment would be impractical, if not impossible. A person of ordinary skill in the art can implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

Aspects.

The following aspects of the disclosure are exemplary only and not intended to limit the scope of the disclosure.

1. A calibration system configured to reduce lab-to-lab or instrument-to-instrument variability of Multi-Attribute Methods (MAM) via run-time signal intensity calibration, the calibration system comprising: a first MAM-based instrument including a first detector, the first MAM-based instrument having a first instrument condition defined by at least one of: (1) a first instrument model or (2) a first set of settings, the first MAM-based instrument configured to receive a first sample and a reference standard, and the first MAM-based instrument further configured to, via the first detector, detect a first sample isoform from the first sample and a first reference standard isoform from the reference standard; one or more processors associated with the first MAM-based instrument, the one or more processors associated with the first MAM-based instrument configured to determine, via a first MAM iteration, a first set of correction factors corresponding to the first sample isoform(s), wherein the first set of correction factors is based on the reference standard, and the one or more processors associated with the first MAM-based instrument further configured to determine a first set of sample abundance values corresponding to the first sample isoform(s), wherein the first set of sample abundance values is based on the first set of correction factors; a second MAM-based instrument including a second detector, the second MAM-based instrument having a second instrument condition defined by at least one of: (1) a second instrument model or (2) a second set of settings, wherein the second instrument condition differs from the first instrument condition, the second MAM-based instrument configured to receive a second sample and the reference standard, and the second MAM-based instrument further configured to, via the second detector, detect a second sample isoform from the second sample and a second reference standard isoform from the reference standard; and one or more processors associated with the second MAM-based instrument, the one or more processors associated with the second MAM-based instrument configured to determine, via a second MAM iteration, a second set of correction factors corresponding to the second sample isoform, wherein the second set of correction factors is based on the reference standard, and the one or more processors associated with the second MAM-based instrument further configured to determine a second set of sample abundance values corresponding to the second sample isoform, wherein the second set of sample abundance values is based on the second set of correction factors, and wherein a variance value of the first set of sample abundance values and the second set of sample abundance values is reduced based on the first set of correction factors and the second set of correction factors.

2. The calibration system according to aspect 1, wherein the one or more processors associated with the first MS instrument, via the first MAM iteration, determines a quality attribute.

3. The calibration system according to aspect 2, wherein the quality attribute is any one of: the first sample isoform, a protein, or an identified impurity.

4. The calibration system according to either aspect 2 or aspect 3, wherein the quality attribute defines any one or more of: fragmentation, oxidation, glycation, hydroxylation, sequence variants, isomerization, deamination, C-terminal lysine, O-linked glycans, or N-linked glycans.

5. The calibration system according to any one of the preceding aspects, wherein the one or more processors associated with the first MS instrument are configured to generate a report including the quality attribute.

6. The calibration system according to any one of the preceding aspects, wherein first instrument model differs from the second instrument model.

7. The calibration system according to any one of the preceding aspects, wherein first set of settings differs from the second set of settings.

8. The calibration system according to any one of the preceding aspects, wherein the first set of correction factors is based on an ion intensity value of the first reference standard isoform and a first reference standard abundance value of the first reference standard isoform.

9. The calibration system according to any one of the preceding aspects, wherein the first set of correction factors calibrates a response factor associated with the first set of sample abundance values to determine the ion intensity value of the first sample isoform.

10. The calibration system according to any one of the preceding aspects, wherein the first set of sample abundance values is further based on an ion intensity value of the first sample isoform.

11. The calibration system according to any one of the preceding aspects, wherein the first MAM-based instrument is a mass spectrometric (MS) instrument.

12. The calibration system according to any one of the preceding aspects, wherein the first MAM-based instrument is a triple-quadrupole instrument.

13. The calibration system according to any one of the preceding aspects, wherein one or more processors associated with the first MS instrument are communicatively coupled to the one or more processors associated with the second MS instrument via a computer network.

14. The calibration system according to any one of the preceding aspects, wherein one or more processors associated with the first MAM-based instrument are the one or more processors associated with the second MAM-based instrument.

15. The calibration system according to any one of the preceding aspects, wherein the first MAM-based instrument is situated at a first laboratory at a first geographical location and the second MAM-based instrument is situated at a second laboratory at a second geographical location.

16. A calibration method for reducing lab-to-lab or instrument-to-instrument variability of Multi-Attribute Methods (MAM) via run-time signal intensity calibration, the calibration method comprising: receiving, at a first MAM-based instrument including a first detector, a first sample and a reference standard; detecting, via the first detector, a first sample isoform from the first sample and a first reference standard isoform from the reference standard; determining, via one or more processors associated with the first MAM-based instrument for a first MAM iteration, a first set of correction factors corresponding to the first sample isoform, wherein the first set of correction factors is based on the reference standard; determining, via the one or more processors associated with the first MAM-based instrument, a first set of sample abundance values corresponding to the first sample isoform, wherein the first set of sample abundance values is based on the first set of correction factors, and wherein the first MAM-based instrument includes a first instrument condition defined by at least one of: (1) a first instrument model or (2) a first set of settings; receiving, at a second MAM-based instrument including a second detector, a second sample and the reference standard; detecting, via the second detector, a second sample isoform from the second sample and a second reference standard isoform from the reference standard; determining, via one or more processors associated with the second MAM-based instrument for a second MAM iteration, a second set of correction factors corresponding to the second sample isoform, wherein the second set of correction factors is based on the reference standard; determining, via the one or more processors associated with the second MAM-based instrument, a second set of sample abundance values corresponding to the second sample isoform, wherein the second set of sample abundance values is based on the second set of correction factors, and wherein the second MAM-based instrument includes a second instrument condition defined by at least one of: (1) a second instrument model or (2) a second set of settings, wherein the second instrument condition differs from the first instrument condition, and wherein a variance value of the first set of sample abundance values and the second set of sample abundance values is reduced based on the first set of correction factors and the second set of correction factors.

17. A calibration method for reducing variability of a MAM-based instrument for multiple time periods via run-time signal intensity calibration, the calibration method comprising: receiving, at a MAM-based instrument for a first time period, a first sample and a reference standard; detecting, via a detector of the MAM-based instrument for the first time period, a first sample isoform from the first sample and a first reference standard isoform from the reference standard; determining, via one or more processors for a first MAM iteration for the first time period, a first set of correction factors corresponding to the first sample isoform, wherein the first set of correction factors is based on the reference standard; determining, via the one or more processors via the first MAM iteration for the first time period, a first set of sample abundance values corresponding to the first sample isoform, wherein the first set of sample abundance values is based on the first set of correction factors, and wherein the MAM-based instrument, for the first time period, includes a first instrument condition defined by a first set of settings; receiving, at the MAM-based instrument for a second time period, a second sample and the reference standard; detecting, via the detector of the MAM-based instrument for the second time period, a second sample isoform from the second sample and a second reference standard isoform from the reference standard; determining, via the one or more processors for a second MAM iteration for the second time period, a second set of correction factors corresponding to the second sample isoform, wherein the second set of correction factors is based on the reference standard; and determining, via the one or more processors via the second MAM iteration for the second time period, a second set of sample abundance values corresponding to the second sample isoform, wherein the second set of sample abundance values is based on the second set of correction factors, and wherein the MAM-based instrument, for the second time period, includes a second instrument condition defined by a second set of settings, wherein the second instrument condition differs from the first instrument condition, and wherein a variance value of the first set of sample abundance values and the second set of sample abundance values is reduced based on the first set of correction factors and the second set of correction factors.

18. The calibration system according to aspect 17, wherein the one or more processors determines a quality attribute.

19. The calibration system according to aspect 18, wherein the quality attribute is any one of: the first sample isoform, the second sample isoform, a protein, or an identified impurity.

20. The calibration system according to any one of aspects 17 to 19, wherein the one or more processors are configured to generate a report including the quality attribute.

21. The calibration system according to aspect 1, wherein the variance value of the first set of sample abundance values and the second set of sample abundance values is reduced by at least 25 percent.

22. The calibration method according to aspect 16, wherein the variance value of the first set of sample abundance values and the second set of sample abundance values is reduced by at least 25 percent.

23. The calibration method according to aspect 17, wherein the variance value of the first set of sample abundance values and the second set of sample abundance values is reduced by at least 25 percent.

24. The calibration system according to aspect 1, wherein the first sample is of a proteolytic peptide, the second sample of the proteolytic peptide, and the reference standard is of the proteolytic peptide.

25. The calibration method according to aspect 16, wherein the first sample is of a proteolytic peptide, the second sample of the proteolytic peptide, and the reference standard is of the proteolytic peptide.

26. The calibration method according to aspect 17, wherein the first sample is of a proteolytic peptide, the second sample of the proteolytic peptide, and the reference standard is of the proteolytic peptide.

Additional Disclosure.

As described herein, new calibration systems and methods are provided to determine abundance of each attribute, using the known abundance of each attribute in the reference standard as calibrant. Most quality attributes in the reference standard remain constant throughout the life of the standard and therefore can serve as calibrant to correct for difference between instruments or sample preparation procedures. Since reference standard data is usually collected in a typical MAM method for identity and system suitability purpose, no additional work is needed from the analyst. With this methodology, consistent instrument model is no longer a requirement. At the same time, small changes in digestion procedure between labs, as well as changes through automation, will not significantly affect the assay result.

Classification of Attributes.

Based on whether the abundance of an attribute may change during sample preparation, each attribute is classified, for MAM purposes, into one of three types, including type-1 attributes, type-2 attributes, and type-3 attributes Type-1 attributes do not change during sample preparation. Examples include sequence variants, lysine, and proline hydroxylation, etc. Most glycosylation can be classified into this group, when the samples do not experience extreme low pH during sample preparation.

Type-2 attributes may decrease in abundance during sample preparation. Examples include phosphorylation due to the instability of the modification. Because the reaction (e.g. loss of phosphorylation) substrates of the type-2 attributes are usually minor components (e.g., phosphorylated peptide), the absolute change of type-2 attributes during sample preparation are small. A special type-2 attribute is the remaining N-terminal glutamine. When the N-terminus of a protein is a glutamine residue, it usually cyclizes to form pyroglutamic acid as the major component. The N-terminal glutamine, being the minor component, is considered as the modified form of the pyroglutamic acid in this work. The N-terminal glutamine is a type-2 attribute because cyclization may happen during sample preparation to reduce the abundance of free N-terminal glutamine.

Type-3 attributes may increase in abundance during sample preparation. Type-3 attributes include oxidation, deamidation, aspartic acid isomerization, fragmentation, etc. Because the reaction substrates of type-3 attributes are the major unmodified peptides, their absolute change during sample preparation can be quite high.

As will be discussed later, type-1 and type-2 attributes can often be measured with high precision and low quantitation limit, as the variation in the results is solely or mainly from the LC-MS measurements. Type-3 attributes, on the other hand, have lower precision and higher quantitation limit because variations in sample preparation contribute to the variation of the final results.

Notations.

Notations used herein may be summarized as follows: A represents the abundance of an isoform as a fractional value (or percentage). I represents the measured ion intensity (area under the peak in the selected-ion chromatogram) of an isoform. k represents the response factor, and a represents the correction factor for the response factor. Superscript 0 represents the reference standard (RS). For example, $A^0$ represent the known abundance of an isoform in RS, and $I^0$ represent the measured ion intensity of an isoform in RS. Subscripts 0, 1, 2, . . . i, . . . n represent the n+1 isoforms associated with a specified residue (including the unmodified form). Subscript 0 represents the most abundant isoform (usually the unmodified form). For example, $A_i$ represent the abundance of isoform i, $I_i$ represents the ion intensity of isoform i, $k_i$ represents the response factor of isoform i, and $a_i$ represents the response factor correction factor for isoform i. The value of $a_0$ is defined as 1. The subscript 1 may be omitted in certain Equations when there is only one isoform present other than the major isoform (n=1). Note when isoforms i=0, 1, . . . n are mentioned in this report, they are generally associated with a single residue, regardless of whether this is explicitly stated or not. For example, there can be three isoforms associated with an Asn residue in a peptide, including the unmodified Asn, its deamidated form, and its succinimide form. An oxidized Met residue on the same peptide, however, may belong to a different set of isoforms (e.g., assuming the two modifications are stochastic and therefore independent of each other).

Conventional MAM.

In a conventional MAM method, the abundance of each attribute (e.g., different modification states of an amino acid residue in a peptide) is calculated based on the MS responses (e.g., area under the peak in the selected-ion chromatogram) of the modified peptide and the unmodified peptide with the following conventional assumptions:

1. Within each sample, all isoforms associated with an amino acid residue have the same response factor (ratios of all response factors=1)
2. Artificially induced attribute changes are negligible Assuming an amino acid residue has n+1 modification states (0, 1, . . . , n), there are n+1 peptide isoforms related to the residue of interest. The most abundant isoform, usually the unmodified, is denoted as i=0. The abundance of each isoform is calculated based on the following equation (3):

$$\begin{cases} kA_i = I_i, i = 0, n \\ \sum_{j=0}^{n} A_j = 1 \end{cases} \quad (3)$$

In the above equation (3), k is the response factor for all isoforms of the peptide (e.g., a constant value based on the above conventional assumption 1), and, $A_i$ and $I_i$ are the abundance and MS intensity of isoform i, respectively. The response factor k represents a combination of the both peptide recovery and the MS response of each isoform.

Solving equation (3) yields equation (4):

$$\begin{cases} k = \sum_{j=0}^{n} I_j \\ A_i = \dfrac{I_i}{\sum_{j=0}^{n} I_j} \end{cases} \quad (4)$$

Equation (4) states that the abundance of each isoform is calculated by the MS intensity of the isoform divided by the sum of MS intensities of all isoforms.

Due to the assumptions described above, a conventional MAM method must meet the following requirements:
1. Digestion efficiency must be reproducible.
2. The MS instrument conditions must be the same.
3. Sample preparation must introduce minimal amount of artificial modifications.

In real world, however, the above requirements are difficult to meet, at least for the following reasons:
1. Due to variations of sample preparation procedure, analyst habit, device and reagent quality, etc., peptide recovery may change.
2. Due to differences in MS instrument model, instrument setting and the way the instrument is maintained, response factors for different peptide isoforms may differ.
3. Due to variations of sample preparation procedure, analyst habit, device and reagent quality, as well as instrument condition, the amount of artificially introduced modification may vary.

As a result of the above difficulties of conventional MAM requirements, a new methodology is needed to overcome these challenges to ensure the long-term success of MAM.

Calibrating Response Factors Using the Reference Standard.

In a MAM, a reference standard is typically analyzed in parallel with the samples for system suitability and identity purpose. Because most quality attributes in a reference standard remain constant throughout the life of the standard, the reference standard can serve as a calibrant to correct for difference between instruments or sample preparation procedures. The abundance of each attribute in a reference standard can be either established using a conventional MAM, or an orthogonal method with better accuracy. If the attribute abundance in the reference standard is determined by an analytical method with absolute quantitation, all subsequent MAM analyses of the same attribute also become an absolute measurement after the response factor calibration.

Using the reference standard as a calibrant in each run, most requirements for conventional MAM regarding lab-to-lab and instrument-to-instrument reproducibility can be eliminated. In such embodiments, the conventional two assumptions, as described above herein, are then revised as follows, i.e., the revised assumptions:
1. Within the same LC-MS sequence, ratios of response factors among all isoforms remain constant.
2. Artificially induced attribute changes are negligible.

Note in the first revised assumption, instead of requiring all peptide isoforms to have the same response factor (all response-factor ratios=1) for the life of the product, it only requires the response-factor ratios to be constant within the same LC-MS sequence (same analyst, same instrument, and same day).

With the new revised assumptions, it is no longer assumed that each isoform has the same response factor. Instead, it is assumed that the response factors for isoform i are modified by the same correction factor $a_i$, in both the reference standard and the sample. Therefore the response factor for isoform i in the reference standard is expressed as $a_i k^0$ (where superscript of 0 stands for reference standard), and the response factor for isoform i in the sample is denoted as $a_i k$. After considering both reference standard and the sample, equation (3) becomes equation (5), which is the same as equation (2) described herein:

$$\begin{cases} a_i k^0 A_i^0 = I_i^0, i = 0, n \\ a_i k A_i = I_i, i = 0, n \\ a_0 = 1 \\ \sum_{j=0}^{n} A_j = 1 \end{cases} \quad (5)$$

In some embodiments, the response factor for the reference standard and the sample can be different due to slight difference in sample preparation, difference in instrument sensitivity, etc. Additionally, for the equations to be solvable, factor a for one of the isoforms is generally set to a constant value. It is not important which isoform is set to a constant a. It is a good idea to set it to the most abundant isoform, which is usually the unmodified form ($a_0=1$).

Solving equation (5) yields equation (6), which is the same as equation (1) described herein:

$$\begin{cases} a_i = \dfrac{I_i^0}{I_0^0} \dfrac{A_0^0}{A_i^0}, i = 0, n \\ A_i = \dfrac{I_i / a_i}{\sum_{j=0}^{n} \dfrac{I_j}{a_j}}, i = 0, n \end{cases} \quad (6)$$

Equation (6) can be used to calculate the correction factor for each isoform ($a_i$) based on known attribute abundance in the reference standard ($A_i^0$), and to calculate the abundance of each isoform in the sample ($A_i$). In order for parameters $a_i$ to have well-defined values, the denominators must not be close to zero. Therefore, for successful response factor calibration, each attribute in the reference standard must have high enough abundance ($A_i^0$) to be accurately quantified.

Calibrating Artificial Modifications Using the Reference Standard.

Some attributes, including type-2 attributes such as phosphorylation, and type-3 attributes such as oxidation, deamidation, Asp-isomerization, and fragmentation, can change their abundance during sample preparation, either due to loss of modification due to their instability (type-2), or artificial formation of these modifications (type-3). These artificial changes of attributes cause analyst-to-analyst and day-to-day variability and may be corrected using the reference standard as a calibrant, assuming the extent of these artificial changes are consistent in the same LC-MS sequence.

In embodiments where a factor $b_i$ is used to denote the extent of artificial change for each isoform, then after considering both reference standard and the sample, equation (3) becomes equation (7):

$$\begin{cases} k^0[A_i^0 + b_i S_i^0] = I_i^0, i = 0, n \\ k[A_i + b_i S_i] = I_i, i = 0, n \\ \sum_{j=0}^{n} A_j = 1 \end{cases} \quad (7)$$

In equation (7), $S_i$ represent the substrate of the artificial modification that produces isoform i. For example, for oxidation and deamidation (type-3 attributes), the substrate is the unmodified peptide. For phosphorylation (type-2 attribute), however, the substrate is the modified (phosphorylated) peptide due to possible instability of the modification.

Depending on the nature of the substrate, equation (7) may become complex. For example, use equation (7) for multiple modifications on the same residue, such as N-glycosylation on asparagine residues, may create a complex variant of equation (7).

For residues with single modification, equation (7) may be reduced to equation (8) and/or equation (9), as described herein, depending on whether the substrate is the modified peptide (type-2) or unmodified peptide (type-3). As shown in the embodiments below, for equations (8) and (9), the equation portions on the right are the solutions of equation portions on the left.

In particular, for type-2 attributes, and with respect to equation (8):

$$\begin{cases} k^0(1 - A^0 - bA^0) = I_0^0 \\ k^0(A^0 + bA^0) = I^0 \\ k(1 - A - bA) = I_0 \\ k(A + bA) = I \end{cases} \rightarrow \begin{cases} b = \dfrac{I^0}{A^0(I_0^0 + I^0)} - 1 \\ A = \dfrac{I}{(1+b)(I_0 + I)} \end{cases} \rightarrow A = \dfrac{I(I_0^0 + I^0)}{(I_0 + I)I^0} A^0 \quad (8)$$

For type-3 attributes, and with respect to equation (9):

$$\begin{cases} k^0[1 - A^0 - b(1 - A^0)] = I_0^0 \\ k^0[A^0 + b(1 - A^0)] = I^0 \\ k[1 - A - b(1 - A)] = I_0 \\ k[A + b(1 - A)] = I \end{cases} \rightarrow \begin{cases} b = \dfrac{\dfrac{I^0}{I_0^0 + I^0} - A^0}{1 - A^0} \\ A = \dfrac{\dfrac{I}{I_0 + I} - b}{1 - b} \end{cases} \quad (9)$$

In equation (8), if the amount of artificial modification is much smaller than the unmodified form (i.e., $b \ll 1$), which is usually true for most type-2 attributes, then equation (8) can be estimated as equation (10):

$$\begin{cases} k^0(1 - A^0) = I_0^0 \\ (1 + b)k^0 A^0 = I^0 \\ k(1 - A) = I_0 \\ (1 + b)kA = I \end{cases} \quad (10)$$

Equation (10) is similar to equation (5), when $a_1=1+b$. That is, in such embodiments, the loss of modification during digestion can be modeled by response factor calibration, and equations (8) and (5) will generate a very similar result.

In order for parameter b and attribute abundance A to have well-defined values, the denominators must not be close to zero. Therefore, to use equation (8), the abundance of the attribute in the reference standard ($A^0$) must be much greater than 0. To use equation (9), $A^0$ must be much less than 1 (100%), and b must not be close to 1. In addition, for equation (9) to be generally meaningful, the value of b must be much smaller than the abundance of the attribute without calibration ($b<<I/(I_0+I)$). Otherwise the calibrated abundance A will be close to zero and sometime a negative value.

Calibrating Both Response Factors and Artificial Modifications Using Two Different Standards.

The reference standard can be used to correct either the response factor (a) (i.e., "a-calibration") and/or artificial modification (b) (i.e., "b-calibration"). An additional standard is needed to correct for both a and b. To get a different standard, the reference standard or another sample can be stressed to create another standard containing higher level of the attributes of interest, and then both standards are analyzed together with the samples. Known attribute abundance of the two standards and their determined MS responses can be used to correct for both a and b.

A superscript of zero may be used to represent the reference standard and a superscript of 1 may be used to represent the stressed standard, when considering both standards as well as the sample. Equations (11) and (12) illustrate representative equations, depending on the substrate of the artificial modification. Note equations (11) and (12) apply to residues with a single modification.

For type-2 attributes, and with respect to equation (11):

$$\begin{cases} k^0[1-A^0-bA^0]=I_0^0 \\ ak^0[A^0+bA^0]=I^0 \\ k^1[1-A^1-bA^1]=I_0^1 \\ ak^1[A^1+bA^1]=I^1 \\ k[1-A-bA]=I_0 \\ ak[A+bA]=I \end{cases} \rightarrow \begin{cases} a = \dfrac{I^0I^1(A^1-A^0)}{I_0^0I^1A^0 - I^0I_0^1A^1} \\ b = \dfrac{I^0}{A^0(aI_0^0+I^0)} - 1 \\ A = \dfrac{I(aI_0^0+I^0)}{I^0(aI_0+I)}A^0 \end{cases} \quad (11)$$

For type-3 attributes, and with respect to equation (12):

$$\begin{cases} k^0[1-A^0-b(1-A^0)]=I_0^0 \\ ak^0[A^0+b(1-A^0)]=I^0 \\ k^1[1-A^1-b(1-A^1)]=I_0^1 \\ ak^1[A^1+b(1-A^1)]=I^1 \\ k[1-A-b(1-A)]=I_0 \\ ak[A+b(1-A)]=I \end{cases} \rightarrow \begin{cases} a = \dfrac{I_0^0I^1(1-A^1) - I^0I_0^1(1-A^0)}{I_0^0I_0^1(A^1-A^0)} \\ b = \dfrac{1}{1-A^0}\left(\dfrac{I^0}{aI_0^0+I^0} - A^0\right) \\ A = \dfrac{1}{1-b}\left(\dfrac{I}{aI_0+I} - b\right) \end{cases} \quad (12)$$

As shown above for equations (11) and/or (12), in order for parameters a and b to have well-defined values, the denominator must not be close to zero. Therefore, equation (11) requires $I_0^0I^1A^0 >> I_0^1I^0A^1$, and equation (12) requires $A^1 >> A^0$ and $A^0 << 1$. Similar to equation (9), for equation (12) to be meaningful, the value of b must be much smaller than the abundance of the attribute without b-calibration ($b<<I/(aI_0+I)$), otherwise the calibrated abundance A will be close to zero and sometime a negative value.

Example of Multi-Attribute Analysis of Anti-Streptavidin IgG2.

As described herein, various example embodiments have been reduced to practice via particular applications of the calibration systems and methods of the present disclosure. It is to be understood, however, that the calibration systems and methods of the present disclosure are not limited to the particular applications. For example, recombinant anti-streptavidin IgG2 was expressed from a Chinese hamster ovary (CHO) cell line. The anti-streptavidin IgG2 material was used as the reference standard. To create test samples for analysis, the reference standard was incubated at approximately 40° C. for about 30 days to create a sample 1, and then samples 2 and 3 were created by mixing sample 1 with the reference standard at different ratios (see Table 2).

The IgG2 reference standard and test samples (~120 µg each) were digested with trypsin using the following procedure. First, each sample was treated with 8 mM dithiothreitol at approximately 25° C. for about 30 minutes under a denaturing solution containing 6.5 M guanidine hydrochloride (Macron Fine Chemicals, Stroudsburg, Pa.) and 0.2 M Tris (TEKnova, Hollister, Calif.) at pH 7.5 to reduce the disulfide bonds. The reduced IgG2 was then alkylated with 14 mM iodoacetic acid at approximately 25° for about 20 minutes in a dark environment. The alkylation reaction was quenched with 6 mM DTT.

To intentionally create some difference in the sample preparation procedure, each reduce/alkylated sample was digested with trypsin using two different methods. In a first method, the reduced/alkylated sample (~1.2 mg/mL IgG2 concentration) was exchanged into the digestion buffer containing approximately 0.1 M Tris and approximately 50 mM methionine (pH 7.5) using a Bio-Rad (Hercules, Calif.) Bio-Spin® 6 column, e.g., according to a manufacturer's recommended procedure. After buffer exchange, appropriate amount of trypsin was added to achieve an enzyme:substrate ratio of approximately 1:12, followed by incubation at approximately 37° C. for about 60 minutes. Digestion was quenched using equal volume of approximately 0.25 M acetate buffer (pH 4.8) in 8 M guanidine hydrochloride. Final IgG2 concentration in the digest was ~0.5 mg/mL.

In a second method, each reduced/alkylated sample was exchanged into the same digestion buffer using a Microcon-30 kDa filter (Millipore Sigma, Burlington, Mass.). First, each reduced/alkylated sample was spun down at approximately 14000 g, and the flow-through was discarded. In certain embodiments, the process was repeated three more times after adding 250 µL of digestion buffer each time to the filter. Trypsin digestion was carried out on the same filter by adding 140 µL digestion buffer and 10 µg trypsin (at 1 mg/mL), followed by incubating at approximately 37° C. for about 60 minutes. After digestion equal volume of quench solution was added to the filter and was spun down at approximately 14000 g to collect peptides in a new receiving tube. Final IgG2 concentration in a digest according to the above procedure yields ~0.4 mg/mL.

Table 2 shows the anti-streptavidin IgG2 samples used in the examples.

TABLE 2

| Sample name | Description |
| --- | --- |
| Reference Standard | Anti-streptavidin IgG2 (30 mg/mL) |
| Sample-1 | Anti-streptavidin IgG2 stressed at 40° C. for 30 days (also used as $2^{nd}$ standard for calibrating both a and b) |
| Sample-2 | 10% Sample-1 + 90% Reference Standard |
| Sample-3 | 20% Sample-1 + 80% Reference Standard |

In anti-streptavidin IgG2 and/or similar embodiments, each digest was analyzed on each of the three LC-MS/MS systems composed of an Agilent (Santa Clara, Calif.) HPLC system connected to a mass spectrometer, e.g., either a Thermo Scientific Q Exactive Plus Biopharma or an Orbitrap Fusion Lumos mass spectrometer. Additional or alternative systems was used as well, such as the disclosure herein in not limited to any one type of system, mass spectrometer, or otherwise. In some embodiments, to purposely introduce some difference in the liquid chromatography conditions, two different LC methods was used (see Table 3).

For a first LC method (e.g., systems A and B in Table 3), peptides were eluted on a Waters (Milford, Mass.) Acquity peptide CSH column (150×2.1 mm, 1.7 μm particle, 170 Å pore size) at a flow rate of approximately 0.3 mL/min with the column temperature maintained at approximately 60° C. Mobile phase A was 0.1% formic acid in water, and mobile phase B was 0.1% formic acid in acetonitrile. After an initial hold at approximately 0.5% B for about 5 minutes, mobile phase B generally linearly increases to approximately 35% in about 40 minutes. Column wash was achieved by increasing mobile phase B to approximately 99% in about 4 minutes with hold for about 1 minute. The column was equilibrated with approximately 0.5% B for about 15 minutes. For a second LC method (e.g., system C in Table 3), peptides were eluted on a Waters Acquity BEH C18 column (2.1×150 mm, 1.7 μm particle) at a flow rate of approximately 0.3 mL/min with the column temperature maintained at about 60° C. Mobile phase A was 0.1% formic acid and about 0.02% trifluoroacetic acid (TFA) in water, and mobile phase B was 0.1% formic acid and 0.02% TFA in acetonitrile. After an initial hold at approximately 0.5% B for about 5 minutes, phase B generally linearly increases to approximately 40% in about 40 minutes. Column wash was achieved by increasing phase B to approximately 99% in about 4 minutes with hold for about 1 minute. The column was equilibrated with approximately 0.5% B for about 15 minutes.

The HPLC systems was directly connected to a mass spectrometer, e.g., either a Thermo Scientific Q Exactive Plus Biopharma mass spectrometer (e.g., system A) or a Thermo Scientific Orbitrap Fusion Lumos mass spectrometer (e.g., systems B and C) through an electrospray interface. While the embodiments herein describe Thermo Scientific Q Exactive Plus Biopharma mass spectrometer and/or Thermo Scientific Orbitrap Fusion Lumos mass spectrometer, it is to be understood that similar mass spectrometer(s) can be used in accordance with the embodiments disclosed herein. The Q Exactive Plus Biopharma was set up to perform full-scan MS at a resolution of about 70,000 and AGC=1×10$^6$, followed by five data-dependent MS/MS (Higher-energy collisional dissociation (HCD) normalized collision energy=27) for most abundant ions. For the Fusion Lumos, full-scan MS data were collected with a resolution of about 60,000 and AGC=4×10$^5$, followed by top speed data-dependent MS/MS in ion-trap (CID normalized collision energy=30). Instrument control and data collection were accomplished by analysis software, e.g., Thermo Scientific Xcalibur software. About 3 to 4 μg of each tryptic digest was injected for analysis. Of course, similar software as the Xcalibur software can be used in accordance with the embodiments disclosed herein.

LC-MS/MS Data were processed on analysis software, MassAnalyzer, as available from Thermo Scientific as BiopharmaFinder™). Analysis software, such as MassAnalyzer, is capable of performing feature extraction, retention time alignment, peptide identification, and attribute quantitation in a fully automated fashion. For peptide identification, analysis software, e.g., MassAnalyzer, may rely on the comparison of experimental MS/MS to the accurately predicted theoretical MS/MS. A matched window function was used to extract the selected-ion chromatogram to maximize the signal-to-noise ratio in the chromatogram. As a final output, analysis software, e.g., MassAnalyzer may create a list of identified variants It is to be understood that similar analysis software as MassAnalyzer can be used in accordance with the embodiments disclosed herein.

Example of Multi-Attribute Analysis of a Fusion Protein.

A recombinant fusion protein (e.g., a first protein, or fragment of a protein is recombinantly fused to at least a second protein, or fragment thereof, often with linkers connecting the proteins/fragments), expressed from CHO cells can contain multiple glycosylation sites, such as on threonine and serine residues. These O-glycans may contribute the most to the heterogeneity of the molecule. In this example, the multi-attribute method was used to quantify these glycoforms in a fusion protein.

For proteolytic digestion, the fusion protein was first denatured in a solution containing approximately 7.5 M guanidine HCl, approximately 250 mM tris (pH 7.5), and approximately 2 mM EDTA, at a protein concentration of approximately 1 mg/mL. Prior to proteolytic digestion, approximately 2 μl of 500 mM DTT solution was added to approximately 100 μL of denatured protein solution, followed by incubation at approximately 25° C. for about 30 minutes to reduce the disulfide bonds. Then, approximately 4 μL of 500 mM sodium iodoacetate was added, followed by incubation at about 25° C. for about 20 minutes, to alkylate the cysteine side chains. After buffer-exchanging into 100 mM tris, 50 mM methionine, pH 7.5 solution by a Bio-Rad Bio-Spin desalting column, every 50 μg of desalted sample was digested with approximately 5 μg of trypsin at approximately 37° C. for about 30 minutes. To quench the digestion, approximately 2% formic acid was added to each digest for a final acid concentration of approximately 0.2%.

Each tryptic digest (~3 μg) was analyzed using an LC-MS system composed of an Agilent HPLC directly connected to a mass spectrometer, e.g., a Thermo Scientific Exactive plus or Q Exactive plus high-resolution mass spectrometer (see Table 3). Peptides were eluted on an Agilent Zorbax C18 RR HD column (2.1×150 mm, 1.8 μm particle, 300 Å pore size) at a flow rate of approximately 0.2 mL/min with the column temperature maintained at 50° C. Mobile phase A was approximately 0.1% formic acid in water, and mobile phase B was 0.1% formic acid in acetonitrile. Beginning with approximately 1.0%, mobile phase B linearly increased to approximately 40% after about 70 minutes and to approximately 90% at about 76 minutes. After washing at approximately 90% for about 5 minutes, the column was equilibrated with approximately 1% B for about 11 minutes. Full-scan MS data was collected at a resolution of 140,000 and the automatic gain control (AGC) target was set to 1×10. Instrument control and data collection were accomplished, e.g., by Thermo Scientific Chromeleon software.

Data were analyzed, e.g., by Thermo Scientific Pinpoint and Chromeleon software for identification and relative quantitation of post-translational modifications. A list of O-glycopeptides was characterized by MS/MS using HCD and electron-transfer dissociation (ETD), where six glycoforms are generally found. Pinpoint can generate a workbook with the accurate mass and isotopic distributions for the six forms of O-glycopeptides. The workbook was imported into Chromeleon software, where it targeted MS1 precursor ions by retention time, accurate mass, as well as isotopic distribution. Selected-ion chromatogram was constructed in Chromeleon, and each peak was integrated for peak area. Integration of each peak was confirmed manually to ensure accuracy.

Table 3 illustrates example LC-MS systems and measurements as described.

TABLE 3

| System | MS | HPLC | HPLC column | HPLC method* |
|---|---|---|---|---|
| Anti-streptavidin IgG2 | | | | |
| A | Q Exactive Plus Biopharma | Agilent 1290 | Waters peptide CSH at 60° C. | Additive: 0.1% formic acid Gradient: 0.5% to 35% of AcN in 40 min Flowrate: 0.3 mL/min |
| B | Fusion Lumos | Agilent 1290 | Waters peptide CSH at 60° C. | Additive: 0.1% formic acid Gradient: 0.5% to 35% of AcN in 40 min Flowrate: 0.3 mL/min |
| C | Fusion Lumos | Agilent 1200 | Waters BEH C18 at 60° C. | Additive: 0.1% formic acid + 0.02% TFA Gradient: 0.5% to 40% of AcN in 40 min Flowrate: 0.3 mL/min |
| Fc-fusion protein | | | | |
| D | Q Exactive Plus Biopharma | Agilent 1290 | Agilent Zorbax C18 RR HD (2.1 × 150 mm, 1.8 μm particle, 300 Å) at 50° C. | Additive: 0.1% formic acid Gradient: 1% to 40% of AcN in 70 min Flowrate: 0.2 mL/min |
| E | Exactive Plus (unit 1) | Agilent 1290 | | |
| F | Exactive Plus (unit 2) | Agilent 1290 | | |

Example of Response Calibration.

Response calibration was performed using analysis software, such as Microsoft® (Redmond, Wash.) Excel®, configured to implement one or more equations described herein. Anti-streptavidin related data were processed by analysis software, e.g., MassAnalyzer. Since MassAnalyzer directly outputs the uncalibrated abundance of each attribute and these uncalibrated abundances are proportional to the corresponding MS intensities (peak areas), they were treated as MS intensities in corresponding calculations. Fc-fusion protein data were processed using Thermo Scientific Chromeleon, in which the peak area of each attribute was determined and used as MS intensities for corresponding calculations. It is a common practice that the reference standard sample is analyzed at least twice (to bracket the samples). To reflect real-world performance, an average MS intensity of two reference standard runs was used in a calculation.

Example of Measurement of a Large Number of Attributes in Anti-Streptavidin IgG2.

In this example, a comprehensive assessment of the performance of calibration systems and methods, as disclosed herein, was demonstrated. An anti-streptavidin IgG2 reference standard was incubated at approximately 40° C. for about four weeks. Then approximately 10% and approximately 20% of this stressed sample was spiked into the reference standard, respectively, to create two more test samples (see, e.g., Table 2). Such test samples, together with both the reference standard as well as the stressed sample, were digested with trypsin in triplicate with two different protocols, and each digest was analyzed on three different LC-MS systems (see, e.g., A, B, and C shown in Table 3) with different columns, mobile phases, gradients, and mass spectrometers. In addition, the reference standard and the stressed sample were each analyzed on system A six times and the average measured abundance of each attribute was used as the reference abundance. All data were processed by analysis software, e.g., MassAnalyzer, to obtain the uncalibrated abundance of each peptide isoform. These abundances were used as MS intensities for further calibration.

Since systems A and B use the same chromatographic condition, data from these runs (e.g., 60 LC-MS/MS runs in total) are processed together because they have consistent retention times. For example, a total of 177 quality attributes were identified and quantified to be above the detection limit (e.g., as indicated by non-zero peak area in all 60 runs). Such attributes cover a wide range of abundance levels, including from 0.001% to 39%. Such attributes included sequence variants, hydroxylation, N-linked and O-linked glycans, N-terminal and C-terminal variants, fragmentation, glycation, oxidation, deamidation, succinimide formation, etc. Fragmentations were distinguished from nonspecific activity of trypsin from their increased level in the stressed sample (e.g., t-test p-value<0.005 and fold-change>2.0 when compared to the reference standard runs).

Example of Calibrating Response Factors (a-Calibration).

Figure 6:
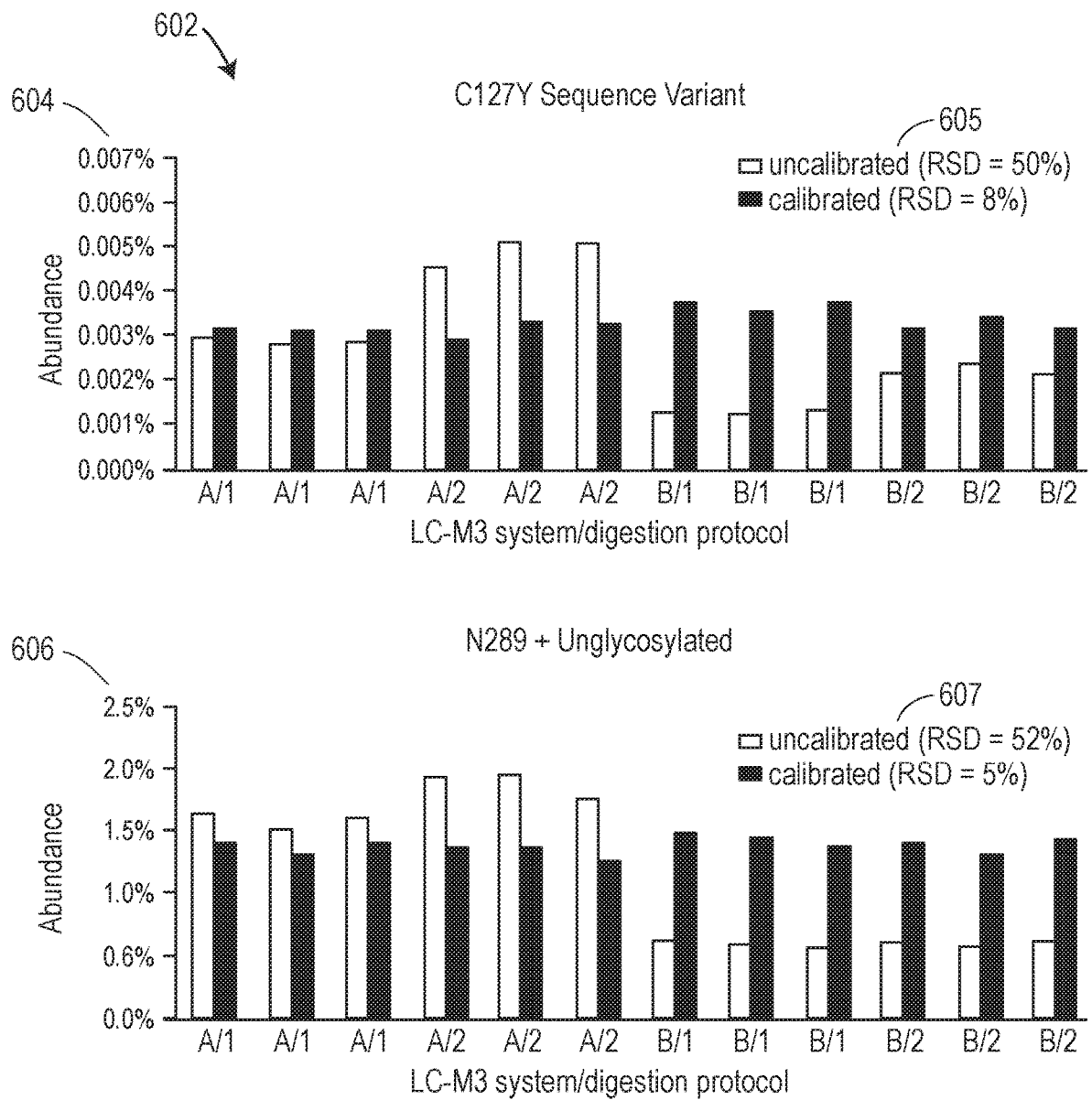
FIG. 6 illustrates a diagram of measured abundances of two attributes in a sample on two different instrument setups and two different sample preparation procedures in accordance with various embodiments disclosed herein.

Using the reference standard for response factor calibration (see equations (5) and (6)), the abundances of each of the 177 attributes in the three samples were calculated. FIG. 6 illustrates a diagram 602 of measured abundances of two attributes in sample-2 on two different instrument setups and two different sample preparation procedures. After response factor calibration, as described herein, the variations caused by difference in sample preparation and instrument setup are greatly reduced, as indicated by the relative standard deviation (RSD) of the 12 measurements of FIG. 6 (i.e., A/1, A/2, B/1, and B/2). In particular, the embodiment of FIG. 6 depicts measured abundance in sample-2, with and without response factor calibration, of heavy chain Cys127Tyr sequence variant (top) (604) and unglycosylated Asn289 (bottom) (606) by two LC-MS systems (e.g., A and B) and two digestion protocols (/1 and /2). After response factor calibration (see equation (6)) the variations between instruments and sample preparation procedures are greatly reduced, as indicated by the RSD values 605 and 607.

Figure 7:
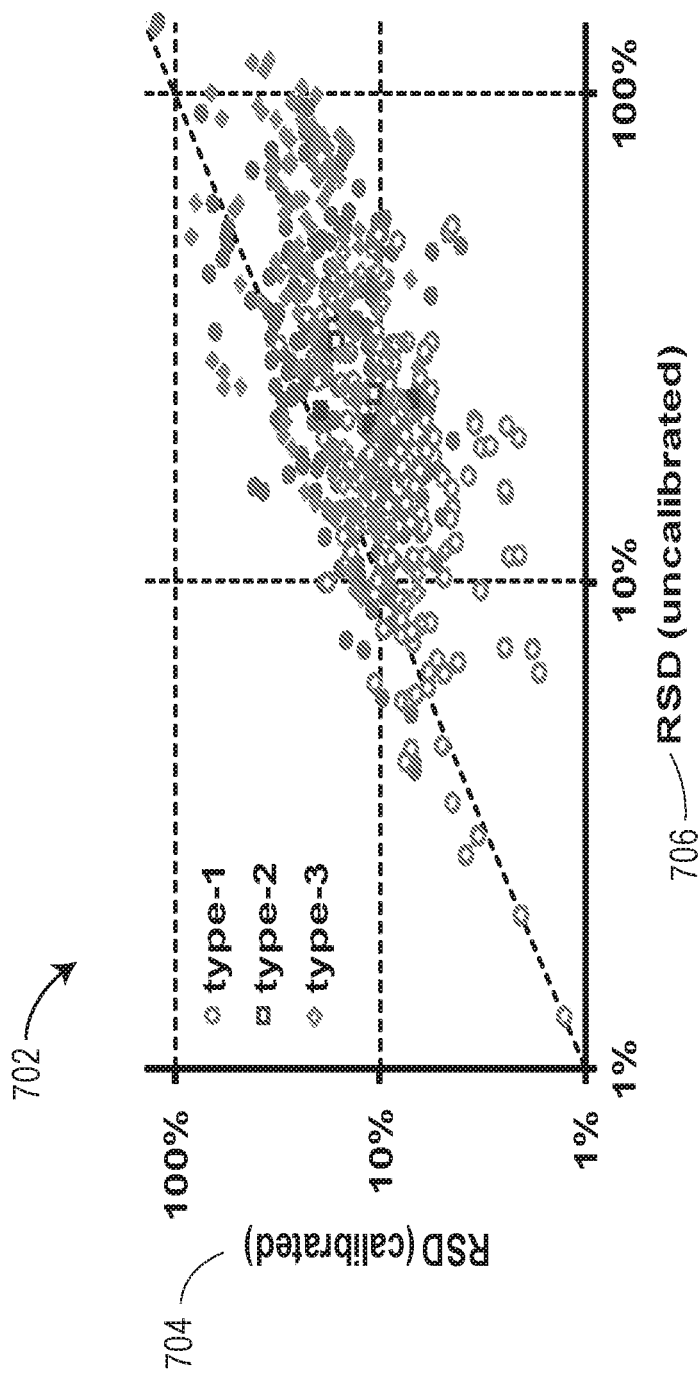
FIG. 7 illustrates a diagram depicting an example comparison of intermediate precision with and without response factor calibration in accordance with various embodiments disclosed herein.

FIG. 7 illustrates a diagram 702 depicting an example comparison of intermediate precision (e.g., indicated by RSD) with (704) and without (706) response factor calibration (see Equation (6)) for the three attribute types. As shown in FIG. 7, intermediate precision is greatly improved after calibration for approximately 86% of the monitored attributes. The shape of the values of FIG. 7 represent the type of attributes, and the open shape values represent attributes with high enough abundance in the reference standard to be precisely quantified (intra-sequence RSD<10%).

In particular, FIG. 7 shows the determined RSD (from 12 measurements with two digestion protocols and two instrument setups as shown in FIG. 6) of all 177 attributes (120 type-1, 12 type-2, and 45 type-3 attributes) in the three samples, with (704) and without (706) the response factor calibration. FIG. 7 represents a total of 177×3=531 data points, each with 12 measurements. RSD of the majority (457, or 86%) of the data points decrease after response factor calibration. Out of the 531 data points, the number of points having RSD<10% increased from 64 (12%) before calibration to 205 (39%) after calibration. Among these, in the embodiment of FIG. 7, type-1 attributes increased from 55 to 171, type-2 attributes from 2 to 36, and type-3 attributes from 7 to 19. Among these 205 data points with good intermediate precision (RSD<10%), 83% (171 out of 205) are type-1 attributes.

As discussed previously, response factor calibration requires that the abundance of the attribute in the reference standard is generally high enough to be accurately quantified. In FIG. 7, attributes with abundance higher than 10-fold of standard deviation (intra-sequence RSD<10%) are marked with open shape values. For example, at least in the embodiment of FIG. 7, most attributes that have RSD below 10% after calibration have high abundance in the reference standard (i.e., open shape values).

Example of Calibrating Artificial Modifications (b-Calibration).

For embodiments regarding type-2 and type-3 attributes, variations in artificial modifications between different sample preparation conditions can be calibrated using equation (8) for type-2 attributes, and equation (9) for type-3 attributes.

Figure 8:
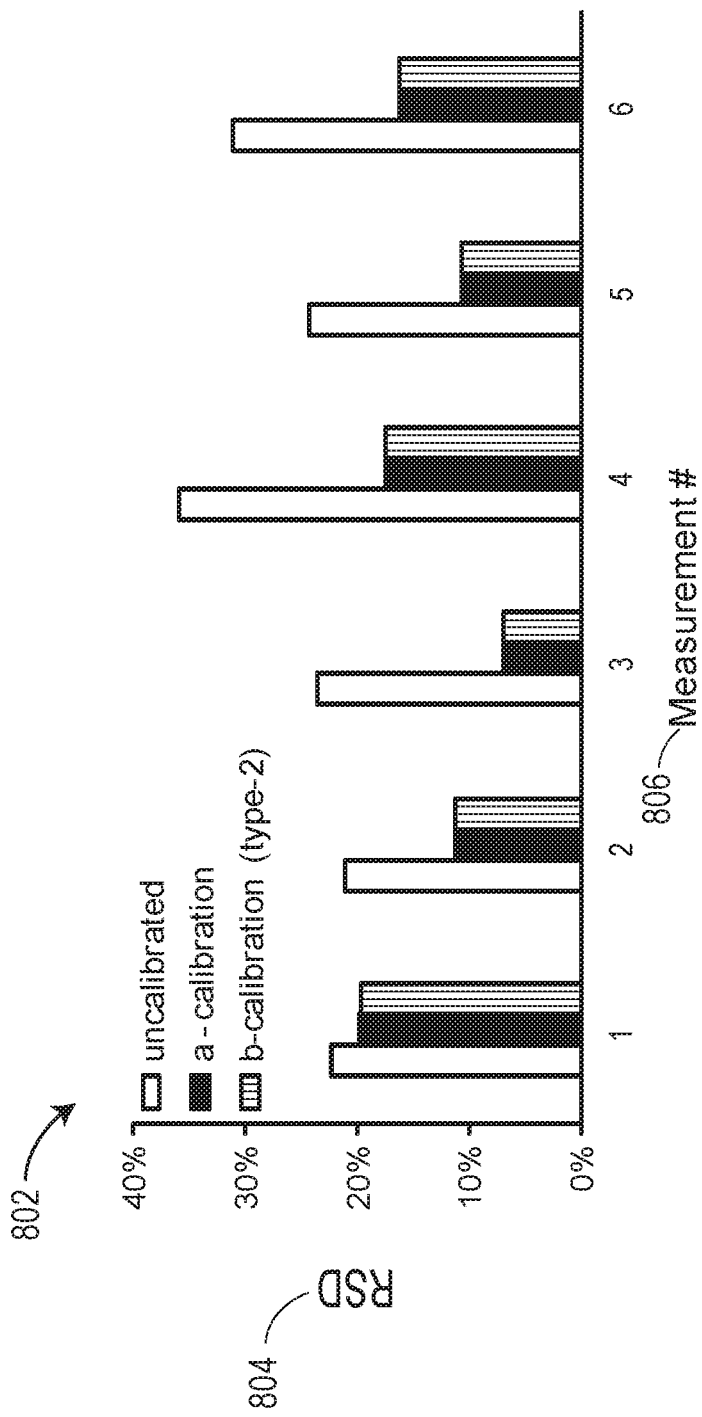
FIG. 8 illustrates a diagram of an embodiment of a calibration of artificial modification for type-2 attributes showing similar results as response factor a-calibration in accordance with various embodiments disclosed herein.

For example, FIG. 8 illustrates a diagram 802 of an embodiment of a calibration of artificial modification for type-2 attributes showing similar results as response factor a-calibration. Specifically, FIG. 8 illustrates an improvement in intermediate precision of type-2 attributes (e.g., two attributes in three samples generated six measurements (806)) after calibration, which is compared to the RSD (804) after response factor calibration. In accordance with embodiments described herein, the two calibration methods generated very similar RSD.

Figure 9:
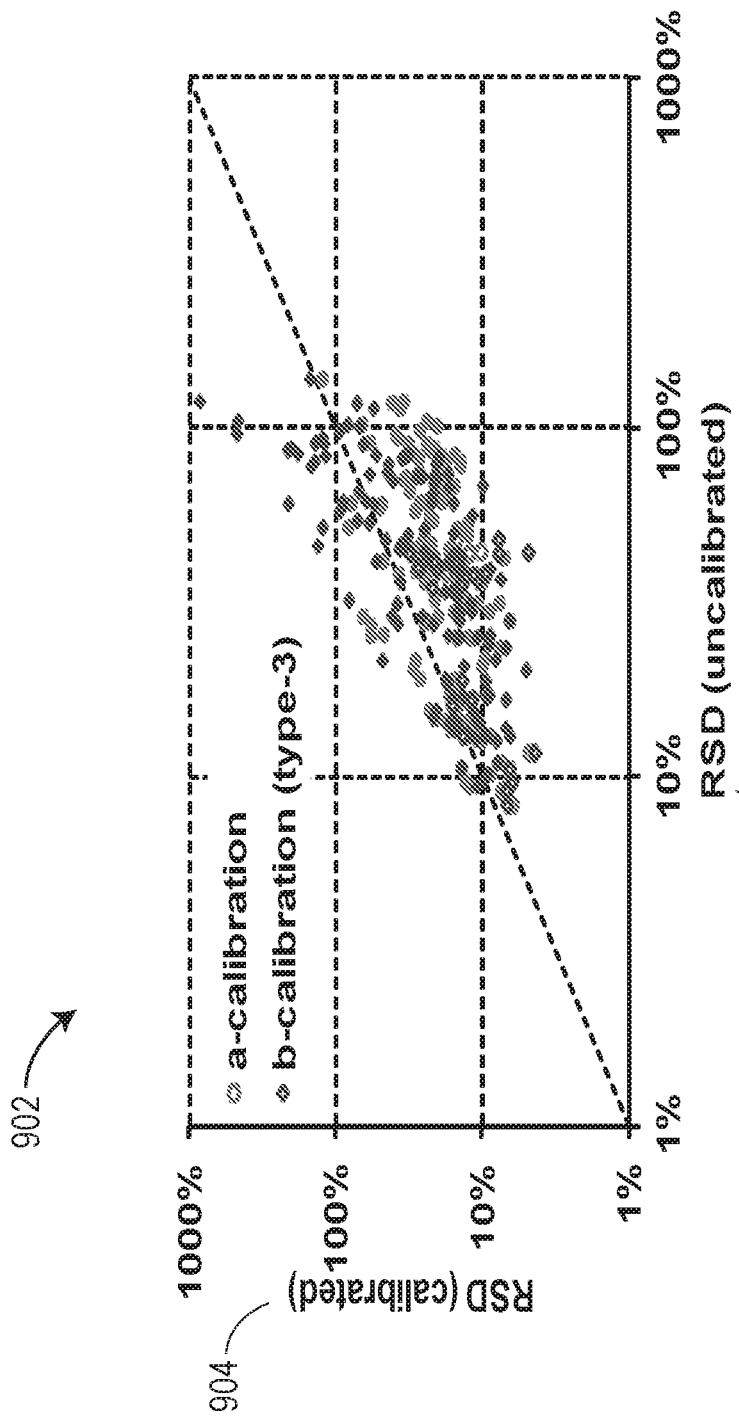
FIG. 9 illustrates a diagram of performance of artificial modification b-calibration for type-3 attributes, compared to response factor a-calibration, in accordance with various embodiments disclosed herein.

FIG. 9 illustrates a diagram 902 of performance of artificial modification b-calibration for type-3 attributes, compared to response factor a-calibration. As illustrated by FIG. 9, for type-3 attributes, calibration (904) of artificial modifications improved intermediate precision for most measurements. For attributes with the calibration parameter b close to the uncalibrated attribute abundance $I/(I_0+I)$, the calibrate abundance A (see equation (9)) will be so close to zero that it may significantly affect the RSD values. For a fair comparison between different calibration methods, the RSD was calculated by dividing the standard deviation of the calibrated abundance by the average a-calibrated attribute abundance. Comparing to response factor calibration (a-calibration), artificial modification calibration (b-calibration) yielded similar performance when the uncalibrated RSD (906) is below 50%. When the uncalibrated RSD is above 50%, b-calibration performance may become less effective compared to a-calibration, and when the uncalibrated RSD is close to 100%, calibrating artificial modifications makes the result less consistent (e.g., higher RSD).

Example of Calibrating Both Response Factors (a) and Artificial Modifications (b).

Figure 10:
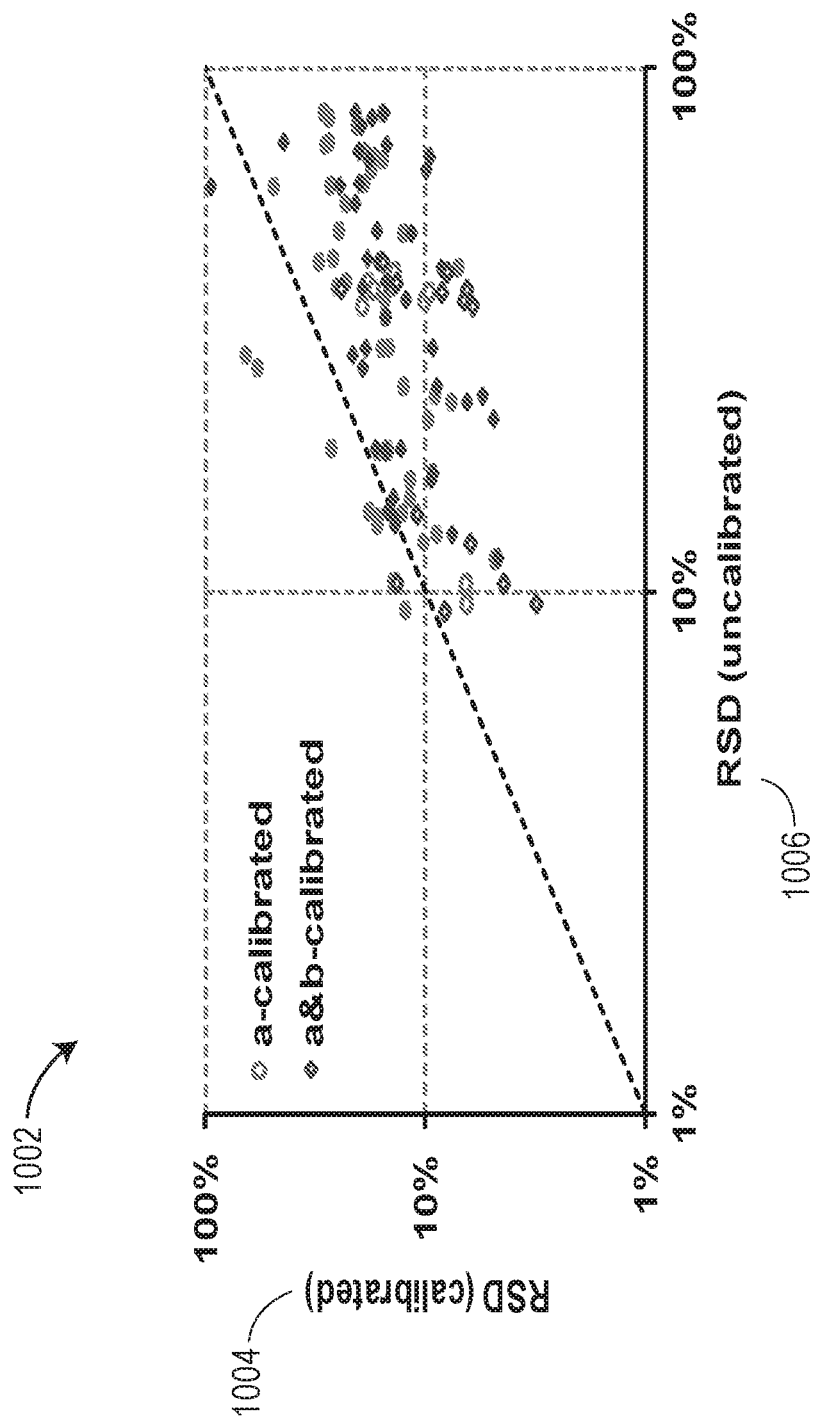
FIG. 10 illustrates a diagram of an embodiment showing performance of two-standard calibration (a&b) for type-3 attributes, compared to one-standard response factor (a) calibration, in accordance with various embodiments disclosed herein.

In some embodiments, both response factor and artificial modification can be calibrated for type-3 attributes, when the second standard is readily available by stressing the reference standard. FIG. 10 illustrates a diagram 1002 of an embodiment showing performance of two-standard calibration (a&b) for type-3 attributes, compared to one-standard response factor (a) calibration. In particular, FIG. 10 shows the performance of the calibration (1004), compared to no calibration (1006), using the reference standard and the stressed sample (sample 1) as the two standards, and sample 2 and 3 as the samples. The RSD was calculated by dividing the standard deviation of the calibrated abundance by the average a-calibrated attribute abundance. FIG. 10 demonstrates that the performance of the two-standard calibration is in general better than the single-standard response factor calibration, but the extent of improvement may be small and, in such circumstances, but not all, may not justify maintaining a second reference standard for the life of a given product.

Example Response Factor Calibration with Data Generated from Very Different LC-MS systems.

Figure 11:
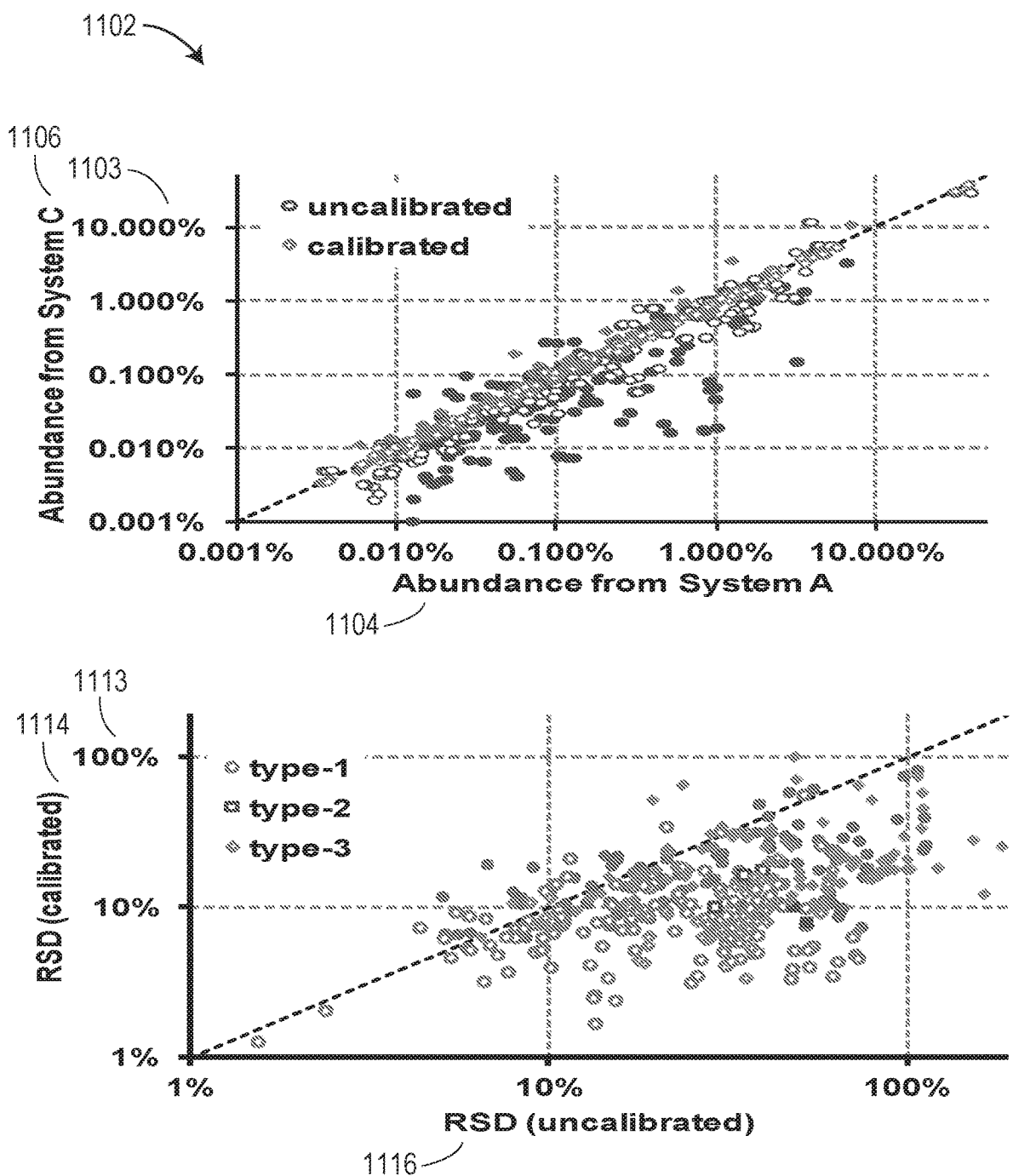
FIG. 11 illustrates a diagram depicting an improvement made in the consistency of two datasets collected on two different LC-MS systems by response factor calibration in accordance with various embodiments disclosed herein.

FIG. 11 illustrates a diagram 1102 depicting an improvement made in the consistency of two datasets collected on two different LC-MS systems by response factor calibration. In particular, FIG. 11 illustrates comparing the determined attribute abundances by system A (1104) and system C (1106) with (1114) and without (1116) response factor calibration. FIG. 11 further illustrates comparing the intermediate precision (RSD) of both datasets with and without calibration. As depicted in FIG. 11, open shape values represent attributes with abundance at least 10-fold of standard deviation in the reference standard (e.g., intra-sequence RSD<10%).

Said another way, FIG. 11 illustrates the performance of response factor calibration based on LC-MS data analysis, where the LC-MS data is collected using two different LC methods and two different MS systems (System A (1104) and C (1106)), with sample preparation performed by two different procedures. In the embodiment of FIG. 11, the determined attribute abundances were compared to each other with (1114) and without (1116) response factor calibration.

Analyzing samples using a different method can detect and identify a different set of attributes, as shown in FIG. 11, among which 117 are in common. In FIG. 11, measurement of the 117 attributes in three samples yielded 351 data points and respective determined abundances by the two methods, with and without a-calibration. Such values are illustrated in FIG. 11 (top graph) (1103). As shown in FIG. 11, calibration greatly improved the consistency of the measurement, even if the two LC-MS systems were completely different. FIG. 11 (bottom graph) (1113) shows the improvement in intermediate precision after response factor calibration for these 117 attributes. Many of these attributes can be precisely measured with the same instrument and method (indicated by open shape values).

When such attributes are measured on a different system, however, the results were not consistent, as indicated by large RSD values from 10% to 100% in the horizontal axis (uncalibrated). Most of these measurements became consistent again after calibration, as indicted by their RSD values less than 10% on the vertical axis.

Example Glycan Profile of a-Fusion Protein.

In this example, a fusion protein containing two O-linked glycosylation sites with six different glycoforms. A sample with unknown glycoform abundance, together with the reference standard, was analyzed in four runs by three analysts on three LC-MS systems (see Table 3). All data were processed on Chromeleon, to get peak areas of each peptide of interest. The abundance of each glycoform was quantified using a conventional method (equation (4)) as well as response factor calibration (equation (6)). To determine the abundance of each attribute in the reference standard, the reference standard was analyzed by conventional MAM six times, and the average value of the six measurements was used as the known abundance in the reference standard.

Figure 12:
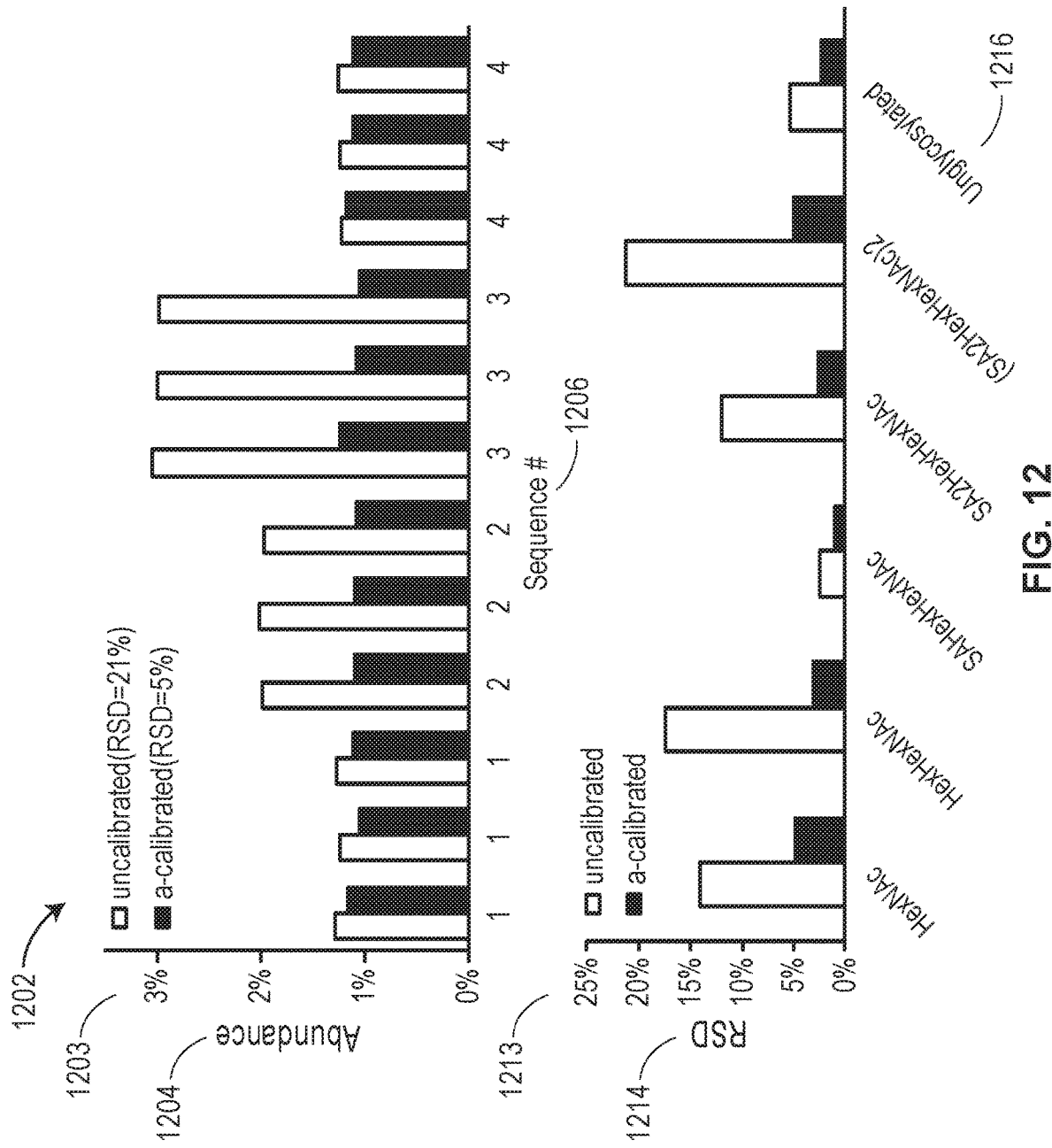
FIG. 12 illustrates a diagram showing measured abundance of glycoform in four sequences, each in triplicate, in accordance with various embodiments disclosed herein.

FIG. 12 illustrates a diagram 1202 showing measured abundance (1204) of glycoform (SAHexHexNAc) in the four sequences (1206), each in triplicate. After response factor calibration (equation (6)), the instrument-to-instrument variation was greatly reduced. Also as shown in FIG. 12 (bottom graph), response factor calibration for the six glycoforms (1216) reduced RSD (1214) from a maximum of 21% to a maximum of 5% (SA: sialic acid or N-acetyl-neuraminic acid; Hex: hexose; HexNAc: N-acetyl-hexosamine). In particular, FIG. 12 (top graph) (1203) shows the 12 measured abundances (triplicate analysis in 4 sequences 1206) for one of the glycoforms with and without response factor calibration. Although the measured abundances were very reproducible within the same sequence, such measured abundances varied significantly between sequences. Response factor calibration eliminated the instrument-to-instrument variation. FIG. 12 (bottom graph) (1213) compares the intermediate RSD for all six glycoforms without and with calibration. The RSD for these glycoforms was between 2.4% and 21% without calibration. After calibration they were reduced to no more than 5%.

Calibration.

In some, but not all, embodiments, calculating attribute abundances using the calibration methods may require additional measurement of ion intensities of each isoform in the reference standard. These additional measurements may introduce additional errors in the final attribute abundance calculation. Improvement in intermediate precision may be achieved if the errors caused by these additional measurements are smaller than the variation between laboratory and instrument.

In some, but not all, embodiments, to enable improvement in measurement precision after calibration, ion intensity of each isoform in the reference standard must be determined. This requires that the attribute of interest must have high enough abundance in the reference standard. As a general rule, the attribute abundance should be at least ten times the standard deviation of the measurement (e.g., shown as open shape values in FIGS. 7, 8, 9, and 10 as described herein).

For embodiments involving type-3 b-calibration (equation (9)), calculation of attribute abundance A may involve taking the difference between the uncalibrated attribute abundance $I/(I_0+I)$ and b. If the value of b is close to $I/(I_0+I)$, calculation of A then involves taking a difference of two large numbers to derive a very small number, potentially generating large errors. In extreme cases, the value of b may be larger than $I/(I_0+I)$ and a negative value of A is obtained. This may make b-calibration for type-3 attributes less robust. The same is true of a&b-calibration for type-3 attributes shown in equation (12).

In some embodiments, the difference in response factors, which include both digestion efficiency and instrument response, may be the primary concern because evolvement of HPLC and MS instrumentation, as well as automation in sample preparation, is inevitable. Artificial modifications can usually be controlled (as described herein) and is less a concern. Therefore, when comparing the three calibration methods, response factor calibration (a-calibration) is generally most favored due to its robustness and applicability to attributes of all three types. Artificial modification calibration (b-calibration) on type-3 attributes, although capable of correcting inconsistencies in sample preparation not corrected by a-calibration, is generally less robust when the level of correction is close to the attribute abundance. In some embodiments, the b-calibration on type-2 attribute, due to the similarity in mathematics, produce similar results as a-calibration and therefore can be replaced by a-calibration. Calibration with two standards for both response factor and artificial modification (a&b-calibration), on the other hand, may, in some, but not all embodiments, is less practical due to the requirement of an additional standard for the life of the product. Additionally, two more ion intensity measurements may be needed with a&b-calibration, which further increases the variance of the final attribute abundance result. Therefore, calibration of the response factor using a single standard is generally used for implementing the new MAM systems and methods as described herein in a cGMP environment.

The new MAM systems and methods are significantly advantageous over conventional MAM because the new MAM systems and methods greatly reduce the lab-to-lab variability through run-time response calibration. The new MAM systems and methods effectively eliminate the requirement of MAM to use consistent equipment, which is a major problem in the current MAM workflow. In addition, because a reference standard is generally already required to be analyzed in parallel with the sample in the current workflow, no additional work is needed from the analyst.

As described herein, using equation (6) for calibrating response factors eliminates the requirement of different peptide isoforms to have the same response factor. The new MAM systems and methods, therefore, may be used for other types of instrumentation for MAM. For example, due to the requirement of equivalent response factors for different isoforms by conventional MAM, selected-reaction monitoring (SRM) on a triple-quadrupole instrument is unacceptable due to potentially very different fragmentation efficiencies among peptide isoforms. The new MAM systems and methods, on the other hand, make it possible to take advantage of triple-quadrupole instruments because such new MAM systems and methods do not require different peptide isoforms to have equivalent response factors. The abundance of each attribute in the reference standard, however, must be established initially on a high-resolution instrument.

One drawback of conventional MAM methodology is that the measured attribute abundance is not absolute, due to the assumption that all isoforms have the same response factors, which may not be true for modifications that involve change in charge, hydrophobicity or peptide length. This drawback is usually not generally a major problem, as long as the response factors are consistent throughout the life of the method. However, when the attribute abundance in the reference standard is determined by a technique with absolute quantitation, attribute abundance determined from the new MAM methodology also becomes an absolute value.

Figure 13:
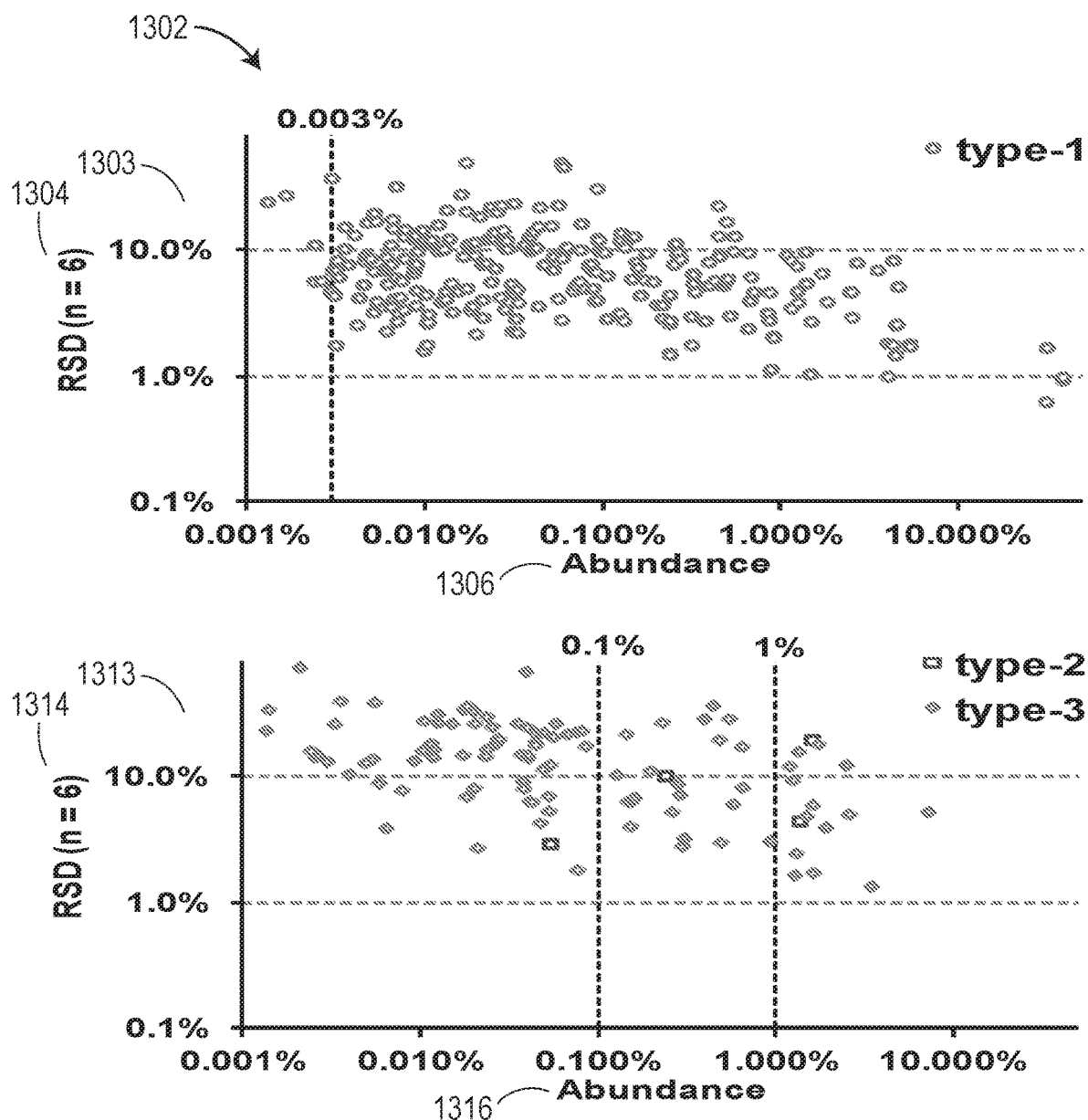
FIG. 13 illustrates a diagram showing the relationship of attribute abundance and intra-sequence RSD for three attribute types, in accordance with various embodiments disclosed herein.

Data as shown for various embodiments herein may also be used to generate insights regarding the limit of quantitation (LOQ) of a MAM platform. LOQ can be defined as the minimum concentration of an attribute with RSD below 10%. For example, FIG. 13 illustrates a diagram 1302 showing the relationship of attribute abundance (1306 and/ or 1316) and intra-sequence RSD (1304 and/or 1314) for the three attribute types. In the embodiment of FIG. 13, for type-1 attributes (top diagram) (1303), the RSD (1304) for most attributes are below 10% at abundances (1306) as low as 0.003% (LOQ=0.003%), when the minor isoform is well resolved from other major peptides. If the isoform is not well resolved from a major peak, the LOQ will be higher due to limited intra-scan dynamic range of the mass spectrometers used in this work. For type-2 and type-3 attributes (bottom diagram) (1313), however, most attributes below 0.1% have RSD (1314)>10% and most attributes above 1% have RSD (1314)<10%, suggesting that the LOQs are typically between ~0.1% and ~1%, depending on the amount of variations introduced during sample preparation.

In particular, FIG. 13 shows the relationship of attribute abundance (1306 and/or 1316) and intra-sequence RSD (n=6) (1304 and/or 1314) for different attribute types. For a majority of type-1 attributes of FIG. 13 (top diagram) (1303), intra-sequence RSDs are below 10%, with abundance down to 0.003%, indicating the quantitation limit of the LC-MS system is as low as 0.003% when the attribute does not change during sample preparation. Also as shown in FIG. 13 (bottom diagram) (1313), quantitation limits are much higher (0.1-1%) for most type-2 and type-3 attributes.

Additional Aspects.

The following additional aspects of the disclosure are exemplary only and not intended to limit the scope of the disclosure. The following additional aspects may be considered as part of, in addition to, or separate from, other aspects of this disclosure, including, by way of non-limiting example, to any of aspects 1 to 26 as described herein.

27. A calibration system configured to reduce lab-to-lab or instrument-to-instrument variability of Multi-Attribute Methods (MAM) via run-time signal intensity calibration, the calibration system comprising: a first MAM-based instrument including a first detector, the first MAM-based instrument having a first instrument condition defined by at least one of: (1) a first instrument model or (2) a first set of settings, the first MAM-based instrument configured to receive a first sample and a reference standard, and the first MAM-based instrument further configured, via the first detector, to detect a first sample isoform from the first sample and a first reference standard isoform from the reference standard, wherein the first sample has a first preparation type; one or more processors associated with the first MAM-based instrument, the one or more processors associated with the first MAM-based instrument configured to determine, via a first MAM iteration, a first set of correction factors corresponding to the first sample isoform, wherein the first set of correction factors is based on the reference standard, and the one or more processors associated with the first MAM-based instrument further configured to determine a first set of sample abundance values corresponding to the first sample isoform, wherein the first set of sample abundance values is based on the first set of correction factors; a second MAM-based instrument including a second detector, the second MAM-based instrument having a second instrument condition defined by at least one of: (1) a second instrument model or (2) a second set of settings, wherein the second instrument condition differs from the first instrument condition, the second MAM-based instrument configured to receive a second sample and the reference standard, and the second MAM-based instrument further configured to, via the second detector, detect a second sample isoform from the second sample and a second reference standard isoform from the reference standard, wherein the second sample has a second preparation type, and wherein the first preparation type differs from the second preparation type causing a variance between the first sample and the second sample, the variance caused by an artificial change of attribute abundance during sample preparation; and one or more processors associated with the second MAM-based instrument, the one or more processors associated with the second MAM-based instrument configured to determine, via a second MAM iteration, a second set of correction factors corresponding to the second sample isoform, wherein the second set of correction factors is based on the reference standard, and the one or more processors associated with the second MAM-based instrument further configured to determine a second set of sample abundance values corresponding to the second sample isoform, wherein the second set of sample abundance values is based on the second set of correction factors, and wherein a variance value of the first set of sample abundance values and the second set of sample abundance values is reduced based on the first set of correction factors and the second set of correction factors, wherein at least one of (1) the one or more processors associated with the first MAM-based instrument, via the first MAM iteration, or (2) the one or more processors associated with the second MAM-based instrument, via the second MAM iteration, determines a quality attribute to reduce the variance between the first sample and the second sample, the quality attribute associated with a type-2 attribute or a type-3 attribute.

28. The calibration system according to aspect 27, wherein the type-2 attribute causes a decrease in abundance during preparation of the first sample or the second sample.

29. The calibration system according to aspect 27, wherein the type-3 attribute causes an increase in abundance during preparation of the first sample or the second sample.

30. A calibration method for reducing lab-to-lab or instrument-to-instrument variability of Multi-Attribute Methods (MAM) via run-time signal intensity calibration, the calibration method comprising: receiving, at a first MAM-based instrument, a first sample and a reference standard, the first MAM-based instrument including a first detector, and the first MAM-based instrument having a first instrument condition defined by at least one of: (1) a first instrument model or (2) a first set of settings; detecting, by the first detector of the first MAM-based instrument, a first sample isoform from the first sample and a first reference standard isoform from the reference standard, wherein the first sample has a first preparation type; determining, by one or more processors associated with the first MAM-based instrument, via a first MAM iteration, a first set of correction factors corresponding to the first sample isoform, wherein the first set of correction factors is based on the reference standard; determining, by the one or more processors associated with the first MAM-based instrument, a first set of sample abundance values corresponding to the first sample isoform, wherein the first set of sample abundance values is based on the first set of correction factors; receiving, by a second MAM-based instrument, a second sample and the reference standard, the second MAM-based instrument including a second detector, the second MAM-based instrument having a second instrument condition defined by at least one of: (1) a second instrument model or (2) a second set of settings, wherein the second instrument condition differs from the first instrument condition; detecting, by the second detector of the second MAM-based instrument, a second sample isoform from the second sample and a second reference standard isoform from the reference standard, wherein the second sample has a second preparation type, and wherein the first preparation type differs from the second preparation type causing a variance between the first sample and the second sample, the variance caused by an artificial change of attribute abundance during sample preparation; determining, by one or more processors associated with the second MAM-based instrument, via a second MAM iteration, a second set of correction factors corresponding to the second sample isoform, wherein the second set of correction factors is based on the reference standard; and determining, by the one or more processors associated with the second MAM-based instrument, a second set of sample abundance values corresponding to the second sample isoform, wherein the second set of sample abundance values is based on the second set of correction factors, wherein a variance value of the first set of sample abundance values and the second set of sample abundance values is reduced based on the first set of correction factors and the second set of correction factors, and wherein at least one of (1) the one or more processors associated with the first MAM-based instrument, via the first MAM iteration, or (2) the one or more processors associated with the second MAM-based instrument, via the second MAM iteration, determines a quality attribute to reduce the variance between the first sample and the second sample, the quality attribute associated with a type-2 attribute or a type-3 attribute.

31. The calibration method according to aspect 30, wherein the type-2 attribute causes a decrease in abundance during preparation of the first sample or the second sample.

32. The calibration method according to aspect 30, wherein the type-3 attribute causes an increase in abundance during preparation of the first sample or the second sample.

33. A calibration system configured to reduce lab-to-lab or instrument-to-instrument variability of Multi-Attribute Methods (MAM) via run-time signal intensity calibration, the calibration system comprising: a first MAM-based instrument including a first detector, the first MAM-based instrument having a first instrument condition defined by at least one of: (1) a first instrument model or (2) a first set of settings, the first MAM-based instrument configured to receive a first sample, a reference standard, and a stressed standard, and the first MAM-based instrument further configured, via the first detector, to detect a first sample isoform from the first sample, a first reference standard isoform from the reference standard, and a stressed reference standard isoform from the stressed standard; one or more processors associated with the first MAM-based instrument, the one or more processors associated with the first MAM-based instrument configured to determine, via a first MAM iteration, a first set of correction factors corresponding to the first sample isoform, wherein the first set of correction factors is based on the reference standard and the stressed standard, and the one or more processors associated with the first MAM-based instrument further configured to determine a first set of sample abundance values corresponding to the first sample isoform, wherein the first set of sample abundance values is based on the first set of correction factors; a second MAM-based instrument including a second detector, the second MAM-based instrument having a second instrument condition defined by at least one of: (1) a second instrument model or (2) a second set of settings, wherein the second instrument condition differs from the first instrument condition, the second MAM-based instrument configured to receive a second sample, the reference standard, and the stressed standard, and the second MAM-based instrument further configured to, via the second detector, detect a second sample isoform from the second sample, a second reference standard isoform from the reference standard, and a second stressed standard isoform from the stressed standard; and one or more processors associated with the second MAM-based instrument, the one or more processors associated with the second MAM-based instrument configured to determine, via a second MAM iteration, a second set of correction factors corresponding to the second sample isoform, wherein the second set of correction factors is based on the reference standard and the stressed standard, and the one or more processors associated with the second MAM-based instrument further configured to determine a second set of sample abundance values corresponding to the second sample isoform, wherein the second set of sample abundance values is based on the second set of correction factors, and wherein a variance value of the first set of sample abundance values and the second set of sample abundance values is reduced based on the first set of correction factors and the second set of correction factors.

34. The calibration system according to aspect 33, wherein the stressed standard contains a higher level of quality attributes than the reference standard.

35. A calibration method for reducing lab-to-lab or instrument-to-instrument variability of Multi-Attribute Methods (MAM) via run-time signal intensity calibration, the calibration method comprising: receiving, at a first MAM-based instrument, a first sample, a reference standard, and a stressed standard, the first MAM-based instrument including a first detector, and the first MAM-based instrument having a first instrument condition defined by at least one of: (1) a first instrument model or (2) a first set of settings; detecting, by the first detector of the first MAM-based instrument, a first sample isoform from the first sample, a first reference standard isoform from the reference standard, and a stressed reference standard isoform from the stressed standard; determining, by one or more processors associated with the first MAM-based instrument, via a first MAM iteration, a first set of correction factors corresponding to the first sample isoform, wherein the first set of correction factors is based on the reference standard and the stressed standard; determining, by the one or more processors associated with the first MAM-based instrument, a first set of sample abundance values corresponding to the first sample isoform, wherein the first set of sample abundance values is based on the first set of correction factors; receiving, at a second MAM-based instrument, a second sample, the reference standard, and the stressed standard, the second MAM-based instrument including a second detector, and the second MAM-based instrument having a second instrument condition defined by at least one of: (1) a second instrument model or (2) a second set of settings, wherein the second instrument condition differs from the first instrument condition; detecting, by the second detector of the second MAM-based instrument, a second sample isoform from the second sample, a second reference standard isoform from the reference standard, and a second stressed standard isoform from the stressed standard; determining, by one or more processors associated with the second MAM-based instrument, via a second MAM iteration, a second set of correction factors corresponding to the second sample isoform, wherein the second set of correction factors is based on the reference standard and the stressed standard; and determining, by the one or more processors associated with the second MAM-based instrument, a second set of sample abundance values corresponding to the second sample isoform, wherein the second set of sample abundance values is based on the second set of correction factors, wherein a variance value of the first set of sample abundance values and the second set of sample abundance values is reduced based on the first set of correction factors and the second set of correction factors.

36. The calibration method according to aspect 35, wherein the stressed standard contains a higher level of quality attributes than the reference standard.

What is claimed is:

1. A calibration system configured to reduce lab-to-lab or instrument-to-instrument variability of Multi-Attribute Methods (MAM) via run-time signal intensity calibration, the calibration system comprising:
   a first MAM-based instrument including a first detector, the first MAM-based instrument having a first instrument condition defined by at least one of: (1) a first instrument model or (2) a first set of settings, the first MAM-based instrument configured to receive a first sample and a reference standard, and the first MAM-based instrument further configured, via the first detector, to detect a first sample isoform from the first sample and a first reference standard isoform from the reference standard;
   one or more processors associated with the first MAM-based instrument, the one or more processors associated with the first MAM-based instrument configured to determine, via a first MAM iteration, a first set of correction factors corresponding to the first sample isoform, wherein the first set of correction factors is based on the reference standard, and the one or more processors associated with the first MAM-based instrument further configured to determine a first set of sample abundance values corresponding to the first sample isoform, wherein the first set of sample abundance values is based on the first set of correction factors;
   a second MAM-based instrument including a second detector, the second MAM-based instrument having a second instrument condition defined by at least one of: (1) a second instrument model or (2) a second set of settings,
   wherein the second instrument condition differs from the first instrument condition,
   the second MAM-based instrument configured to receive a second sample and the reference standard, and the second MAM-based instrument further configured to, via the second detector, detect a second sample isoform from the second sample and a second reference standard isoform from the reference standard; and
   one or more processors associated with the second MAM-based instrument, the one or more processors associated with the second MAM-based instrument configured to determine, via a second MAM iteration, a second set of correction factors corresponding to the second sample isoform, wherein the second set of correction factors is based on the reference standard, and the one or more processors associated with the second MAM-based instrument further configured to determine a second set of sample abundance values corresponding to the second sample isoform, wherein the second set of sample abundance values is based on the second set of correction factors, and
   wherein a variance value of the first set of sample abundance values and the second set of sample abundance values is reduced based on the first set of correction factors and the second set of correction factors.

2. The calibration system of claim 1, wherein the one or more processors associated with the first MAM-based instrument, via the first MAM iteration, determines a quality attribute.

3. The calibration system of claim 2, wherein (A) the quality attribute is any one of: the first sample isoform, a protein, or an identified impurity, (B) the quality attribute defines any one or more of: fragmentation, oxidation, glycation, hydroxylation, sequence variant, isomerization, deamination, C-terminal lysine, O-linked glycan, or N-linked glycan, or (C) the one or more processors associated with the first MS instrument are configured to generate a report including the quality attribute.

4. The calibration system of claim 1, wherein (A) the first instrument model differs from the second instrument model, (B) the first set of settings differs from the second set of settings, (C) the first set of correction factors is based on an ion intensity value of the first reference standard isoform and a first reference standard abundance value of the first reference standard isoform, (D) the first set of correction factors calibrates a response factor associated with the first set of sample abundance values to determine the ion intensity value of the first sample isoform, or (E) the first set of sample abundance values is further based on an ion intensity value of the first sample isoform.

5. The calibration system of claim 1, wherein the first MAM-based instrument is (A) a mass spectrometric (MS) instrument or (B) a triple-quadrupole instrument or (C) situated at a first laboratory at a first geographical location and the second MAM-based instrument is situated at a second laboratory at a second geographical location.

6. The calibration system of claim 1, wherein one or more processors associated with (A) the first MS instrument are communicatively coupled to the one or more processors associated with the second MS instrument via a computer network or (B) the first MAM-based instrument are the one or more processors associated with the second MAM-based instrument.

7. The calibration system of claim 1, wherein the variance value of the first set of sample abundance values and the second set of sample abundance values is reduced by at least 25 percent or the first sample is of a proteolytic peptide, the second sample of the proteolytic peptide, and the reference standard is of the proteolytic peptide.

8. The calibration system of claim 1, wherein the first sample is of a proteolytic peptide, the second sample of the proteolytic peptide, and the reference standard is of the proteolytic peptide.

9. The calibration system of claim 1, wherein the first sample has a first preparation type,
wherein the second sample has a second preparation type, and
wherein the first preparation type differs from the second preparation type causing a variance between the first sample and the second sample, the variance caused by an artificial change of attribute abundance during sample preparation; and
wherein at least one of (1) the one or more processors associated with the first MAM-based instrument, via the first MAM iteration, or (2) the one or more processors associated with the second MAM-based instrument, via the second MAM iteration, determines a quality attribute to reduce the variance between the first sample and the second sample, the quality attribute associated with a type-2 attribute or a type-3 attribute.

10. The calibration system of claim 9, wherein the type-2 attribute causes a decrease in abundance during preparation of the first sample or the second sample or the type-3 attribute causes an increase in abundance during preparation of the first sample or the second sample.

11. The calibration system of claim 1,
the first MAM-based instrument further configured to receive a stressed standard, and the first MAM-based instrument further configured, via the first detector, to detect a stressed reference standard isoform from the stressed standard;
wherein the first set of correction factors is based on the reference standard and the stressed standard,
wherein the second MAM-based instrument is configured to receive the stressed standard, and wherein the second MAM-based instrument is further configured to, via the second detector, detect a second stressed standard isoform from the stressed standard,
and wherein the second set of correction factors is based on the reference standard and the stressed standard.

12. The calibration system of claim 11, wherein the stressed standard contains a higher level of quality attributes than the reference standard.

13. A calibration method for reducing lab-to-lab or instrument-to-instrument variability of Multi-Attribute Methods (MAM) via run-time signal intensity calibration, the calibration method comprising:
receiving, at a first MAM-based instrument including a first detector, a first sample and a reference standard;
detecting, via the first detector, a first sample isoform from the first sample and a first reference standard isoform from the reference standard;
determining, via one or more processors associated with the first MAM-based instrument for a first MAM iteration, a first set of correction factors corresponding to the first sample isoform, wherein the first set of correction factors is based on the reference standard;
determining, via the one or more processors associated with the first MAM-based instrument, a first set of sample abundance values corresponding to the first sample isoform, wherein the first set of sample abundance values is based on the first set of correction factors, and wherein the first MAM-based instrument includes a first instrument condition defined by at least one of: (1) a first instrument model or (2) a first set of settings;
receiving, at a second MAM-based instrument including a second detector, a second sample and the reference standard;
detecting, via the second detector, a second sample isoform from the second sample and a second reference standard isoform from the reference standard;
determining, via one or more processors associated with the second MAM-based instrument for a second MAM iteration, a second set of correction factors corresponding to the second sample isoform, wherein the second set of correction factors is based on the reference standard;
determining, via the one or more processors associated with the second MAM-based instrument, a second set of sample abundance values corresponding to the second sample isoform, wherein the second set of sample abundance values is based on the second set of correction factors, and wherein the second MAM-based instrument includes a second instrument condition defined by at least one of: (1) a second instrument model or (2) a second set of settings,
wherein the second instrument condition differs from the first instrument condition, and
wherein a variance value of the first set of sample abundance values and the second set of sample abundance values is reduced based on the first set of correction factors and the second set of correction factors.

14. The calibration method of claim 13, wherein the variance value of the first set of sample abundance values and the second set of sample abundance values is reduced by at least 25 percent or the first sample is of a proteolytic peptide, the second sample of the proteolytic peptide, and the reference standard is of the proteolytic peptide.

15. The calibration method of claim 13, wherein the first sample has a first preparation type;
wherein the second sample has a second preparation type, and wherein the first preparation type differs from the second preparation type causing a variance between the first sample and the second sample, the variance caused by an artificial change of attribute abundance during sample preparation; and
wherein at least one of (1) the one or more processors associated with the first MAM-based instrument, via the first MAM iteration, or (2) the one or more processors associated with the second MAM-based instrument, via the second MAM iteration, determines a quality attribute to reduce the variance between the first sample and the second sample, the quality attribute associated with a type-2 attribute or a type-3 attribute.

16. The calibration method of claim 15, wherein the type-2 attribute causes a decrease in abundance during preparation of the first sample or the second sample or the type-3 attribute causes an increase in abundance during preparation of the first sample or the second sample.

17. The calibration method of claim 13, further comprising:
receiving, at a first MAM-based instrument, a stressed standard;
detecting, by the first detector of the first MAM-based instrument, a stressed reference standard isoform from the stressed standard, wherein the first set of correction factors is based on the reference standard and the stressed standard;
receiving, at the second MAM-based instrument, the stressed standard;

detecting, by the second detector of the second MAM-based instrument a second stressed standard isoform from the stressed standard; and wherein the second set of correction factors is based on the reference standard and the stressed standard.

18. The calibration method of claim 17, wherein the stressed standard contains a higher level of quality attributes than the reference standard.

19. A calibration method for reducing variability of a MAM-based instrument for multiple time periods via run-time signal intensity calibration, the calibration method comprising:

receiving, at a MAM-based instrument for a first time period, a first sample and a reference standard;

detecting, via a detector of the MAM-based instrument for the first time period, a first sample isoform from the first sample and a first reference standard isoform from the reference standard;

determining, via one or more processors for a first MAM iteration for the first time period, a first set of correction factors corresponding to the first sample isoform, wherein the first set of correction factors is based on the reference standard;

determining, via the one or more processors via the first MAM iteration for the first time period, a first set of sample abundance values corresponding to the first sample isoform, wherein the first set of sample abundance values is based on the first set of correction factors, and wherein the MAM-based instrument, for the first time period, includes a first instrument condition defined by a first set of settings;

receiving, at the MAM-based instrument for a second time period, a second sample and the reference standard;

detecting, via the detector of the MAM-based instrument for the second time period, a second sample isoform from the second sample and a second reference standard isoform from the reference standard;

determining, via the one or more processors for a second MAM iteration for the second time period, a second set of correction factors corresponding to the second sample isoform, wherein the second set of correction factors is based on the reference standard; and determining, via the one or more processors via the second MAM iteration for the second time period, a second set of sample abundance values corresponding to the second sample isoform, wherein the second set of sample abundance values is based on the second set of correction factors, and wherein the MAM-based instrument, for the second time period, includes a second instrument condition defined by a second set of settings, wherein the second instrument condition differs from the first instrument condition, and wherein a variance value of the first set of sample abundance values and the second set of sample abundance values is reduced based on the first set of correction factors and the second set of correction factors.

20. The calibration method of claim 19, wherein the one or more processors determines a quality attribute.

21. The calibration method of claim 20, wherein the quality attribute is any one of: the first sample isoform, the second sample isoform, a protein, or an identified impurity or the one or more processors are configured to generate a report of the quality attribute.

22. The calibration method of claim 19, wherein the variance value of the first set of sample abundance values and the second set of sample abundance values is reduced by at least 25 percent or the first sample is of a proteolytic peptide, the second sample of the proteolytic peptide, and the reference standard is of the proteolytic peptide.

* * * * *